United States Patent [19]

Glicksman et al.

[11] Patent Number: 5,516,772
[45] Date of Patent: May 14, 1996

[54] K-252 DERIVATIVES WHICH ENHANCE NEUROTROPHIN-INDUCED ACTIVITY

[75] Inventors: Marcie A. Glicksman, Swarthmore; Robert L. Hudkins, Chester Springs; David P. Rotella, Dowington; Nicola T. Neff, Rose Valley, all of Pa.; Chikara Murakata, Tokyo, Japan

[73] Assignees: Cephalon, Inc., West Chester, Pa.; Kyowa Hakko Kogyo Co., Ltd., Tokyo, Japan

[21] Appl. No.: 307,530

[22] Filed: Sep. 16, 1994

Related U.S. Application Data

[63] Continuation-in-part of Ser. No. 122,893, Sep. 16, 1993, Pat. No. 5,468,872.

[51] Int. Cl.$^6$ ................................................. A61K 31/40
[52] U.S. Cl. ........................................ 514/211; 514/410
[58] Field of Search ................................. 514/211, 410

[56] References Cited

U.S. PATENT DOCUMENTS

| | | | |
|---|---|---|---|
| 4,735,939 | 4/1988 | McCoy et al. | 514/211 |
| 4,816,450 | 3/1989 | Bell et al. | 514/25 |
| 4,877,776 | 10/1989 | Murakata et al. | 514/43 |
| 4,923,986 | 5/1990 | Murakata et al. | 540/545 |
| 5,093,330 | 3/1992 | Caravatti et al. | 514/211 |
| 5,231,001 | 7/1993 | Kaplan et al. | 435/7.21 |

FOREIGN PATENT DOCUMENTS

| | | | |
|---|---|---|---|
| 328000 | 8/1989 | European Pat. Off. | 548/416 |
| WO94/02488 | 2/1994 | European Pat. Off. | C07D 498/22 |
| 60-257652 | 6/1987 | Japan . | |
| 60-295173 | 7/1987 | Japan . | |
| 60-295172 | 7/1987 | Japan . | |
| 63-295588 | 12/1988 | Japan . | |
| 62-327858 | 12/1988 | Japan . | |
| 62-327859 | 12/1988 | Japan . | |
| WO93/00909 | 1/1993 | WIPO . | |
| WO93/08809 | 5/1993 | WIPO . | |

OTHER PUBLICATIONS

Appel, "A Unifying Hypothesis for the Cause of Amyotrophic Lateral Sclerosis, Parkinsonism, and Alzheimer Disease," Ann. Neurol 10:499–505, 1981.

Berg et al., "K–252a Inhibits Nerve Growh Factor–induced trk Proto–oncogene Tyrosine Phosphorylation and Kinase Activity," The Journal of Biological Chemistry 267:13–16, 1992.

Borasio, "Differential effects of the protein kinase inhibitor K–252a on the in vitro survival of chick embryonic neurons," Neuroscience Letters 108:207–212, 1990.

Bottenstein et al., "Growth of a rat neuroblastoma cell line in serum–free supplemented medium," Proc. Natl. Acad. Sci. USA 76:514–517, 1979.

Bozyczko–Coyne et al., "A rapid fluorometric assay to measure neuronal survival in vitro," Journal of Neuroscience Methods 50:205–216, 1993.

Collazo et al., "Cellular Targets and Trophic Functions of Neurotrophin–3 in the Developing Rat Hippocampus," Neuron 9:643–656, 1992.

Coussens et al., "Multiple, Distinct Forms of Bovine and Human Protein Kinase C Suggest Diversity in Cellular Signaling Pathways," Science 233:859–866, 1986.

Doherty et al., "K–252 a specifically inhibits the survival and morphological differentiation of NGF–dependent neurons in primary cultures of human dorsal root ganglia," Neuroscience Letters 96:1–6, 1989.

Fonnum, "A rapid radiochemical method for the determination of choline acetyltransferase," Journal of Neurochemistry 24:407–409, 1975.

Fraser, "Expression of Eucaryotic Genes in Insect Cell Cultures," In Vitro Cellular & Developmental Biology 25:225–235, 1989.

Glicksman et al., "K–252a and Staurosporine Promote Choline Acetyltransferase Activity in Rat Spinal Cord Cultures," Journal of Neurochemistry 61:210–221, 1993.

Hallböök et al., "Evolutionary Studies of the Nerve Growth Factor Family Reveal a Novel Member Abundantly Expressed in Xenopus Ovary," Neuron 6:845–858, 1991.

Ishida et al., "Effect of Depolarizing Agents on Choline Acetyltransferase and Acetylcholinesterase Activities in Primary Cell Cultures of Spinal Cord," The Journal of Neuroscience 3:1818–1823, 1983.

Kase et al., "K–252 Compounds, Novel and Potent Inhibitors of Protein Kinase C and Cyclic Nucleotide–Dependent Protein Kinases," Biiochemical and Biophysical Research Communications 142:436–440, 1987.

Klein et al., "trkB, a novel tyrosine protein kinase receptor expressed during mouse neural development," The EMBO Journal 8:3701–3709, 1989.

Klein et al., "The trk Proto–Oncogene Encodes a Receptor for Nerve Growth Factor," Cell 65:189–197, 1991.

Knüsel et al., "K–252b Selectively Potentiates Cellular Actions and trk Tyrosine Phosphorylation Mediated by Neurotrophin–3," Journal of Neurochemistry 59:715–722, 1992.

Koizumi et al., "K–252a: A Specific Inhibitor of the Action of Nerve Growth factor on PC12 Cells," The Journal of Neuroscience 8:715–721, 1988.

Laemmli, "Cleavage of Structural Proteins during the Assembly of the Head of Bacteriophage T4," Nature 227:680–685, 1970.

(List continued on next page.)

Primary Examiner—Jacqueline Haley
Attorney, Agent, or Firm—Fish & Richardson; Richard P. Burgoon, Jr.

[57] ABSTRACT

Disclosed are derivatives of the indolocarbazole alkaloid K-252*a* of the Formulae I–VI, useful for enhancing neurotrophin-induced activity of neurotrophin responsive cells. A particularly preferred neurotrophin is NT-3, and a particularly preferred neurotrophin responsive cell is one which comprises a trk receptor. The enhanced neurotrophin-induced activity occasioned by the disclosed K-252a derivatives may be determined by the following assays: ChAT activity; DRG neuronal survival; or cell division (mitogenesis).

9 Claims, 6 Drawing Sheets

OTHER PUBLICATIONS

Lamballe et al., "trkC, a New Member of the trk Family of Tyrosine Protein Kinases, Is a Receptor for Neurotrophin-3," Cell 66:967–979, 1991.

Levi–Montalcini, "Developmental Neurobiology and the Natural History of Nerve Growth Factor," Ann. Rev. Neurosci. 5:341–62, 1982.

Lewis et al., "Is K252a a Non–Competitive Partial Agonist of High Affinity NGF Receptors?" Society for Neuroscience, Abstract, 1:13, 1992.

Maisonpierre et al., "Neurotrophin-3: A Neurotrophic Factor Related to NGF and BDNF," Science 247:1446–51, 1990.

Matsuda et al., "Inhibition by K–252a, a new inhibitor of protein kinase, of nerve growth factor–induced neurite outgrowth of chick embryo dorsal root ganglion cells," Neuroscience Letters 87:11–17, 1988.

McManaman et al., "Developmental Discord among Markers for Cholinergic Differentiation: In Vitro Time Courses for Early expression and Responses to Skeletal Muscle Extract," Developmental Biology 125:311–320, 1988.

Moody et al., "Synthesis of the Staurosporine Aglycon," J. Org. Chem. 57:2105–2114, 1992.

Morrissey, "Silver Stain for Proteins in Polyacrylamide Gels: A Modified Procedure with Enhanced Uniform Sensitivity," Analytical Biochemistry 117:307–310, 1981.

Nakanishi et al., "K–252b, c and d, Potent Inhibitors of Protein Kinase C from Microbial Origin," The Journal of Antibiotics 39:1066–1071, 1986.

Ohmichi et al., "Inhibition of the Cellular Actions of Nerve Growth Factor by Staurosporine and K252A Results from the Attenuation of the Activity of trk Tyrosine Kinase," Biochemistry 31:4034–4039, 1992.

Nye et al., "K–252a and Staurosporine Selectively Block Autophosphorylation of Neurotrophin Receptors and Neurotrophin–Mediated Response," Molecular Biology of the Cell 3:677–686, 1992.

Smith et al., "Molecular Engineering of the Autographa californica Nuclear Polyhedrosis Virus Genome: Deletion Mutations within the Polyhedrin Gene," Journal of Virology 46:584–593, 1983.

Steglich et al., "Indole Pigments from the Fruiting Bodies of the Slime Mold Arcyria denudata," Angew. Chem. Int. Ed. Engl. 19:459–460, 1980.

K-252 DERIVATIVES WHICH ENHANCE NEUROTROPHIN-INDUCED ACTIVITY

This application is a continuation-in-part of U.S. Ser. No. 08/122,893, filed Sep.16, 1993, now U.S. Pat. No. 5,468,872.

BACKGROUND OF THE INVENTION

This invention concerns derivatives of an indolocarbozole alkaloid referred to as "K-252a," and the use of these derivatives to enhance molecular, biological and cellular activities which result from the binding of neurotrophins to cells which comprise neurotrophin receptors.

The cause of neurodegenerative disorders such as Alzheimer's, Parkinson's and Amyotrophic Lateral Sclerosis (ALS or "Lou Gehrig's Disease") is unknown. In recent years, however, it has been hypothesized that alterations in neurotrophin localization, expression levels of neurotrophins, and/or expression levels of the receptors which bind the neurotrophins, may accompany such disorders. Neurotrophins are low molecular weight polypeptides that play a role in the development, function, and/or survival of certain cells, including neurons. The death or dysfunction of neurons have been directly implicated in a number of neurodegenerative disorders.

A variety of neurotrophins have been identified. These include Nerve Growth Factor (NGF), Neurotrophin-3 (NT-3), Neurotrophin-4/5 (NT-4/5), and Brain Derived Neurotrophic Factor (BDNF). Of these, NGF was the first neurotrophin identified and is the best characterized neurotrophin.

NGF is required for the normal development and function of certain sensory and sympathetic neurons. Experimental evidence to date indicates that NGF regulates a variety of cellular responses important to the function of neurons. The present lack of definitive information regarding the in vivo function of other neurotrophins, such as NT-3, has hampered those investigating the causes of neuro degenerative disorders. It is presently known that NT-3 plays a role in the survival and function of cholinergic neurons in basal forebrain. However, as with NGF, NT-3 may also influence the survival and/or function of many different cell types.

It has been suggested that the lack of or inadequate functioning of neurotrophins is linked to neuronal degeneration. This degeneration occurs in disorders such as Alzheimer's, Parkinson's and ALS. Accordingly, it has been suggested that by providing those suffering from such disorders with a corresponding neurotrophic factor, such neural degeneration may be alleviated or prevented. (See, Appel, S. H. 10 *Ann.Neurol.* 499, 1981). For example, it has been suggested that NGF may be useful in the treatment of Alzheimer's because NGF is the trophic factor for the population of basal forebrain cholinergic neurons which degenerate in Alzheimer's patients. As suggested, "adding" NGF to a patient's system may prevent the death of such neurons, or improve the function of such neurons.

Unfortunately, technical and ethical considerations have so far hampered the development of therapeutic agents based upon the neurotrophins. For example, it is technically difficult to produce sufficient quantities of pure neurotrophins using so-called recombinant DNA techniques. Additionally, although it is possible to utilize human fetal cells to produce neurotrophins, the ethical ramifications raised by the use of such cells (typically obtained from an aborted fetus) has all but prevented the utilization of this approach.

Accordingly, the search for a different approach or approaches to the use of neurotrophins in the mediation of disorders or diseases has intensified.

A more refined understanding of the role of the neurotrophins in neurodegenerative disorders would be useful in addressing such approaches. Such an understanding would allow for a more rational design of therapeutics because once the mechanistic relationship between the neurotrophins and a specified disorder is fully appreciated, then defects, flaws or problems in such mechanisms can be more appropriately addressed.

One such approach would involve the development of molecules which "mimic" the effect of the neurotrophins; for example, molecules which bind to neurotrophin receptors, whereby such binding leads to certain cellular responses identical to those achieved when the neurotrophin-like molecule binds to its receptor. Another approach would involve the development of molecules which enhance the response or responses associated with the binding of the neurotrophins to their receptors, i.e., molecules which, in effect, mediate neurotrophin-receptor interaction that is otherwise not viable or is insignificant.

Focusing on the latter approach, it is known that the binding of neurotrophins to their receptors (these receptors are collectively referred to as "trk") leads to the immediate phosphorylation of tyrosine residues on the receptor, referred to as "autophosphorylation". Autophosphorylation is an absolute requirement for the activation of signal transduction pathways which regulate certain molecular responses which can relate to the function and/or survival of cells such as neurons. (See, generally, Klein et al. 65 *Cell* 189, 1991; and Lamballe et al. 66 *Cell* 967, 1991). The trk family of receptors currently comprises trk A, trk B and trk C. Individual trk receptors bind with different subsets of neurotrophins. For example, NGF binds trk A, but not trk B; NT-3 binds primarily trk C, and, to a lesser extent, trk A (however, NT-3 binding to trk A results in little, if any, observable functional activity). The importance of trk A in the trk family and the molecular mechanisms which result from trk A tyrosine kinase activity are manifest because of the putative connection between NGF and certain neurodegenerative disorders.

Maintaining this focus, it would be highly desirable to identify agents which enhance neurotrophin induced activity. Such agents would provide a benefit in further understanding and exploiting the molecular mechanisms of the neurotrophins, as well as for use as therapeutic agents for the treatment of neurodegenerative disorders.

SUMMARY OF THE INVENTION

In its broadest sense, the invention is directed to K-252a derivatives. K-252a is an indolocarbazole alkaloid that was originally isolated from a Nocardiosis sp. culture (Kase et al. 39 *J. Antibiotics* 1059, 1986). K-252a is an inhibitor of several enzymes, including protein kinase C and trk tyrosine kinase (see, Kase et al. 142 *Biochem. Biophys. Res. Comm.* 436, 1987; Nakamishi et al. 263 *J. Biol. Chem.* 6215, 1988; and Berg et al. 267 *J. Biol. Chem.* 13, 1992). Consistent with the inhibition of trk tyrosine kinase activity, K-252a blocks NGF mediated cell survival in some in vitro cell assays, but not in other assay systems (see Kuizumi et al. 8 *J. Neurosci.* 715, 1988; Doherty et al. 96 *Neurosci. Lett.* 11, 1988; but see Borasio 108 *Neurosci. Lett.* 207, 1990). K-252a will induce neurotrophin-like effects in certain neuronal cell types, but the chemically related K-252b will not (see Knusel et al. 59

*J. Neurochem.* 715, 1992). These findings suggest that multiple molecules, including proteins, interact with K-252a (Coussens et al. 233 *Science* 859, 1986). K-252a and K-252b impact the phosphorylation state of trk. For example, K-252a may inhibit neurotrophin-induced receptor autophosphorylation (Squinto et al. WO 93/00909); however, in some settings, K-252a and K-252b potentiate target cell actions and trk tyrosine phosphorylation of trk mediated by NT-3 (see Knusel, supra).

The conflicting data discussed above indicate that an accurate approach in predicting the panoply of K-252a functional activities can not be readily ascertained or predicted. This point is further supported when consideration is given to the proposed uses of K-252a: tumor inhibition (U.S. Pat. Nos. 4,877,776; 5,093,330; European Publication 238,011 in the name of Nomato); anti-insecticidal activity (U.S. Pat. No. 4,735,939); and inhibition of inflammation (U.S. Pat. No. 4,816,450).

We have discovered that certain defined compounds generally described as K252a derivatives (disclosed in detail below) are useful in enhancing neurotrophin-induced activity of neurotrophin responsive cells.

As used herein, the terms "enhance" and "enhancing" when used to modify the phrase "neurotrophin-induced activity" each mean that the combination of a K-252a derivative and a neurotrophin has a comparably greater effect on the induction of an activity than the neurotrophin alone has on the induction of that activity.

As used herein, the phrase "neurotrophin-induced activity" means any response which directly or indirectly results from the binding of a neurotrophin to a neurotrophin responsive cell and which results in the autophosphorylation of neurotrophin-receptor associated tyrosine residues. Most preferably, the neurotrophin receptor is a trk receptor. Exemplary responses which directly or indirectly result from autophosphorylation of neurotrophin-receptor associated tyrosine residues are (i) choline acetyltransferase (CHAT) activity; (2) dorsal root ganglion (DRG) neuron survival; (3) cell division (mitogenesis); or (4) promotion of the survival or function of cholinergic neurons and sensory neurons. These exemplary responses are implicated in the mediation and/or treatment of certain disorders, including (a) Alzheimer's, (b) motor neuron diseases (e.g., ALS, Parkinson's), (c) cerebrovascular disorders (e.g., stroke, ischaemia), (d) Huntington's, (e) AIDS dementia, (f) epilepsy, (g) peripheral neuropathies (e.g., those affecting DRG neurons in chemotherapy-associated peripheral neuropathy), (h) disorders induced by excitatory amino acids, as well as disorders associated with concussive or penetrating injuries of the brain or spinal cord. As such, the K-252a derivatives can be utilized in the mediation and/or treatment of disorders which result from, e.g., the death or dysfunction of cells to which a neurotrophin can bind, e.g., cholinergic, sensory or DRG neurons.

As used in the phrase "neurotrophin-induced activity" the term "neurotrophin" includes both endogenous and exogenous neurotrophin, where "endogenous" refers to a neurotrophin already present and "exogenous" refers to a neurotrophin added to a system. As defined, "neurotrophin-induced activity" includes activity induced by: (1) endogenous neurotrophin; (2) exogenous neurotrophin; and (3) a combination of endogenous and exogenous neurotrophins.

As used herein, the phrase "neurotrophin responsive cell" means a cell which comprises a receptor to which a neurotrophin can specifically bind. Most preferably, the receptor is a trk receptor. Exemplary neurotrophin responsive cells include neurons and non-neuronal cells.

As used herein, the term "trk" refers to the family of high affinity neurotrophin receptors presently comprising trk A, trk B and trk C, and other membrane associated proteins to which a neurotrophin can bind and which binding leads to autophosphorylation of a tyrosine residue associated with such membrane associated protein, and the direct or indirect activation of a functional response.

As used herein, the term "neurotrophin" means a polypeptide that directly or indirectly promotes the survival or function of a cell, such as a neuron. Exemplary neurotrophins include Nerve Growth Factor (NGF), Neurotrophin-3 (NT-3), Neurotrophin-4/5 (NT-4/5) and Brain Derived Neurotrophic Factor (BDNF).

As used herein, the term "neuron" includes cholinergic neurons and sensory neurons. As used herein, the phrase "cholinergic neurons" means neurons in the Central Nervous System (CNS) and Peripheral Nervous System (PNS) whose neurotransmitter is acetylcholine. As used herein, the phrase "sensory neurons" includes neurons responsive to environmental cues (e.g., temperature, movement) from, for example, the skin, muscle and joints of a mammal. Exemplary of a sensory neuron is a neuron from the DRG.

As used herein, the term "K-252a derivative" comprises those compounds which are disclosed in greater detail below; generally, the K-252a derivatives as disclosed herein are chemically modified forms of K-252a.

As outlined in greater detail below, the ability of a K-252a derivative to enhance the neurotrophic-induced activity of a neurotrophin responsive cell can be determined using any of the following assays:

1. basal forebrain neuron ChAT assay; or
2. DRG neuron survival assay; or
3. PC-12 trk tyrosine phosphorylation assay; or
4. trk receptor mitogenesis assay.

ChAT catalyzes the synthesis of the neurotransmitter acetylcholine and is, therefore, considered an enzymatic marker for a functional cholinergic neuron (i.e., a cholinergic neuron which is, or is capable of, surviving or functioning). DRG neuron survival can be assayed in vitro by quantitation of the specific uptake and enzymatic conversion of a dye by living neurons. Phosphorylation of tyrosine can be assessed using PC-12 (a malignant neuronal progenitor cell line derived from a pheochromocytoma) cells; such phosphorylation can be readily detected by immunoprecipitation and blotting of trk by an antibody which recognizes a cytoplasmic domain of trk A, B and C, followed by detection using labelled anti-phosphotyrosine antibody. Mitogenesis, mediated by cell lines separately transfected with trk A, trk B and trk C, allows for analysis of the ability of a K-252a derivative to enhance a neurotrophin-induced activity of a neurotrophin responsive cell (e.g., mitogenesis as mediated by the binding of NT-3 to trk receptors).

Other features and advantages of the invention will be apparent from the following description of preferred embodiments and from the claims.

DESCRIPTION OF THE PREFERRED EMBODIMENTS

The drawings are first described.
Drawings FIG. 1 is a graph which illustrates the dosage effect of NT-3 on ChAT activity in embryonic rat basal forebrain cultures.

Figure 1:
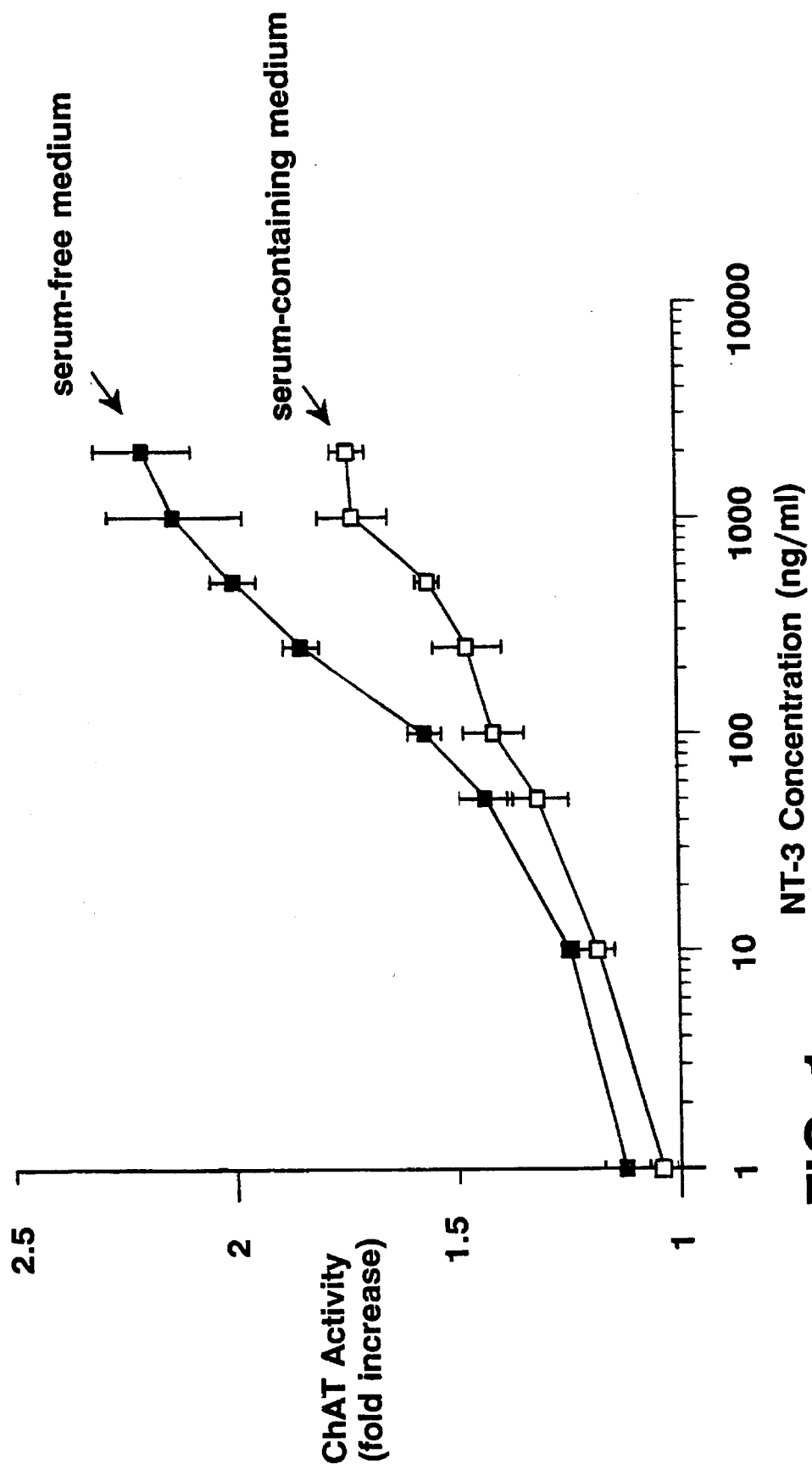

Disclosed herein are K-252a derivatives which are useful in enhancing the neurotrophin-induced activity of neurotrophin responsive cells. In preferred embodiments, at least one type of exogenous neurotrophin is utilized in conjunction with the K-252a derivative; most preferably at least one of the exogenous neurotrophins so utilized is NT-3.

K-252a derivatives as disclosed herein have any of Formulae I–VI.

A. Formula I:

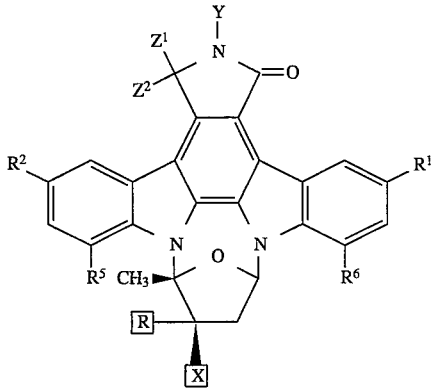

wherein:

a) $Z^1$ and $Z^2$ together represent O; each $R^1$, $R^2$, $R^5$, and $R^6$, independently is H, F, Cl, Br, I, $NO_2$, CN, alkyl of 1–6 carbons, or $NR^{13}R^{14}$ where each $R^{13}$ and $R^{14}$ independently is H or n-alkyl of 1–6 carbons; Y is H, OH, $NH_2$, n-alkyl of 1–6 carbons, CHO, $OCONH_2$ benzyl, O-n-alkyl of 1–6 carbons, $(CH_2)_N OH$ or $(CH_2)_n NH_2$ where n is an integer of 1–6; then either 1) R is OH, OCONH, or O-n-alkyl of 1–6 carbons; and X is $CH_{20}H$, $CH_2NH$, (or an acid salt thereof;) $CH_2$O-n-alkyl of 2–7 carbons, $CO_2R^7$ where $R^7$ is H or alkyl of 1–6 carbons, $CONHOR^8$, $CONH(CH_2)_n OR^8$ where n is an integer of 1–6 and $R^8$ is H or an acyl derivative group, or $CONHR^9$ where $R^9$ is alkyl of 1–3 carbons; or 2) R and X are combined to form a linking group of the formula —$CH_2OCR^{10}R^{11}O$— where each $R^{10}$ and $R^{11}$ independently is H or alkyl of 1–3 carbons; or —$CH_2NR^{12}CO_2$— where $R^{12}$ is H or alkyl of 1–3 carbons;

or b) Z is H and $Z^2$ is OH;

Y is H or CHO;

R is OH; and

X is $CONH(CH_2)_2OH$, $CO_2CH_3$, or $CH_2OH$; and $R^1$, $R^2$, $R^5$ and $R^6$ are as defined in a);

or c) $Z^1$ and $Z^2$ are both H and Y is H, CHO, n-alkyl of 1–6 carbons or $OCONH_2$; then either 1) R is OH, O-n-alkyl of 1–6 carbons or $OCONH_2$, except that when Y is H, R is OH; and X is $CONHOR^8$, $CONH(CH_2)_n OR^8$, where n is an integer of 1–6 carbons, $CH_2OH$, or $CO_2CH_3$, except that when Y is H and $R^1$, $R^2$, $R^5$ and $R^6$ are each H, X cannot be $CO_2CH_3$; or 2) R and X are combined to form a linking group of the formula —$CH_2NR^{12}CO_2$—; and each $R^1$, $R^2$, $R^5$ and $R^6$ are as defined in a), except that when $R^1$ is Br, X cannot be $CH_2OH$;

or d) $Z^1$ is H and $Z^2$ is $SR^{15}$ where $R^{15}$ is n-alkyl of 1–3 carbons; and Y, R and X are defined as in b), except that when $R^{15}$ is CH, X cannot be $CH_2OH$; and $R^1$, $R^2$, $R^5$ and $R^6$ are as defined in a).

B. Formula II:

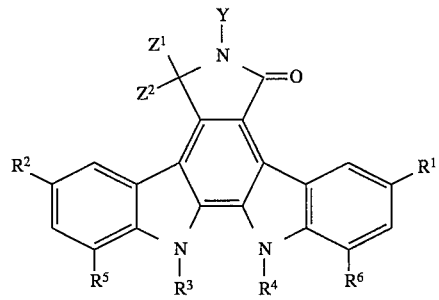

wherein:

a) $Z^1$ and $Z^2$ together represent O, then either 1) each $R^1$, $R^2$, $R^5$, and $R^6$ independently is H, F, Cl, Br, I, NO, CN, alkyl of 1–6 carbons, or $NR^{13}R^{14}$ where each $R^{13}$ and $R^{14}$, independently, is H or n-alkyl of 1–6 carbons; and Y is H, OH, NH, n-alkyl of 1–6 carbons, CHO, benzyl, O-n-alkyl of 1–6 carbons, $(CH_2)_n OH$ or $(CH_2)_n NH_2$ where n is an integer of 1–6; and each $R^3$ and $R^4$ independently is H or $(CH_2)_n CH(OH)CH_2OH$, where n is an integer of 1–6;

or 2) each $R^1$, $R^2$, $R^3$, $R^4$, $R^5$ and $R^6$ independently is H; and Y is as defined in a) 1), except that Y cannot be benzyl;

or b) $Z^1$ is H and $Z^2$ is H, OH, or $SR^{15}$, where $R^{15}$ is n-alkyl of 1–3 carbons;

Y is H or CHO; and each $R^1$, $R^2$, $R^3$, $R^4$, $R^5$, $R^6$ independently is H.

C. Formula III:

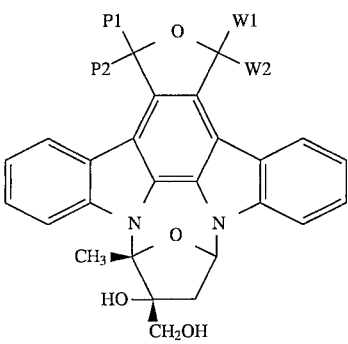

wherein:
a) each P1 and P2 is H or P1 and P2 together represent O; and each W1 and W2 is H or W1 and W2 together represent O; provided that each P1 and P2 is different from W1 and W2.

D. Formula IV:

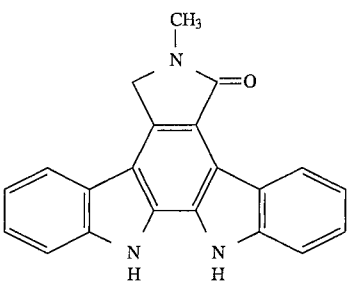

or a pharmaceutically acceptable salt thereof.

E. Formula V:

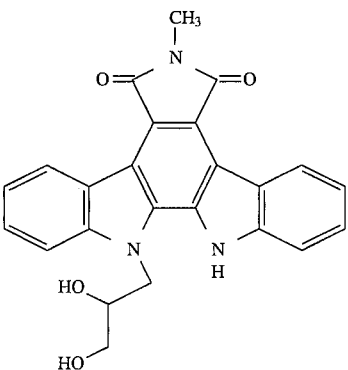

or a pharmaceutically acceptable salt thereof.

F. Formula VI:

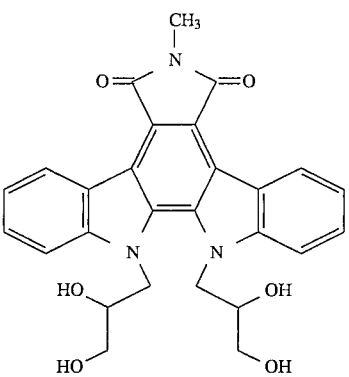

or a pharmaceutically acceptable salt thereof.

Formulae IV, V and VI are species derived from the genus of Formula II.

"Pharmaceutically acceptable salts", as defined herein, are inorganic acid addition salts such as hydrochloride, sulfate, and phosphate; and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminum salt, and zinc salt. Examples of the pharmaceutically acceptable ammonium salts are ammonium salt and tetramethyl ammonium salt. Examples of the pharmaceutically acceptable organic amine addition salts are salts with morpholine and piperidine. Examples of the pharmaceutically acceptable amino acid addition salts are salts with lysine, glycine, and phenylalanine.

Preferred embodiments of the K-252a derivatives are those where the substitutions listed in Table 1 are made (Roman Numeral indicates Formula number from which the species is derived).

TABLE 1

| Compound[1] | Y | X | R | $Z^1Z^{2[2]}$ |
|---|---|---|---|---|
| IV | CHO | — | — | H, H |
| II-2 | H | — | — | O |
| I-1 | H | $CO_2CH_3$ | OH | O |
| I-2 | H | $CO_2$n-$C_3H_7$ | OH | O |
| I-3 | H | $CO_2$n-$C_4H_9$ | OH | O |
| I-4 | H | $CO_2$n-$C_6H_{13}$ | OH | O |
| I-5 | $CH_3$ | $CO_2CH_3$ | $OCH_3$ | O |
| I-6[3] | H | $CO_2CH_3$ | OH | O |
| III-1[7] | — | $CH_2OH$ | OH | — |
| I-7 | H | $CONH(CH_2)_2OH$ | OH | H, H |

TABLE 1-continued

| Compound[1] | Y | X | R | $Z^1Z^{2(2)}$ |
|---|---|---|---|---|
| I-8[6] | H | —CH$_2$OC(CH$_3$)$_2$O— | — | O |
| I-9[6] | NH$_2$ | —CH$_2$OC(CH$_3$)$_2$O— | — | O |
| I-10 | NH$_2$ | CH$_2$OH | OH | O |
| I-11 | H | CONHCH$_3$ | OH | O |
| I-12[6] | H | —CH$_2$NHCO$_2$— | — | O |
| I-13[6] | H | —CH$_2$H(CH$_3$)CO$_2$— | — | O |
| I-14 | CH$_3$ | CH$_2$OH | OH | O |
| I-15 | CH$_2$CH$_2$OH | CH$_2$OH | OH | O |
| V[4] | CH$_3$ | — | — | O |
| VI[5] | CH$_3$ | — | — | O |
| I-16 | NH$_2$ | CH$_2$NH$_2$.HCl | OH | O |
| II-5 | CH$_3$ | — | — | O |
| I-17 | OH | CH$_2$OH | OH | O |
| I-18 | H | CO$_2$CH$_3$ | OH | H, OH |
| I-19 | H | CO$_2$CH$_3$ | OH | H, SC$_2$H$_5$ |
| I-20 | H | CH$_2$OH | — | OHH, OH |
| I-21[6] | H | —CH$_2$N(C$_2$H$_5$)CO$_2$— | — | O |
| I-22 | H | CONHOH | OH | H, H |
| I-23 | CH$_3$ | CO$_2$CH$_3$ | OCH$_3$ | H, H |
| I-24[6] | CH$_3$ | —CH$_2$N(CH$_3$)CO$_2$— | — | H, H |
| I-25 | OCONH$_2$ | CO$_2$CH$_3$ | OCONH$_2$ | H, H |
| III-2[8] | — | CH$_2$OH | OH | — |

[1]R$^1$ and R$^2$ are H except as noted in [3]; R$^5$ and R$^6$ are H; R$^3$ and R$^4$ are H except as noted in [4] and [5].
[2]Z$^1$ and Z$^2$ are as noted, or both are combined together to represent oxygen, where indicated.
[3]R$^1$ and R$^2$ are both Br.
[4]R$^3$ is CH$_2$CH(OH)CH$_2$OH and R$^4$ is H.
[5]R$^3$ and R$^4$ are both CH$_2$CH(OH)CH$_2$OH.
[6]X and R are combined together to form the linking group.
[7]P1, P2 are combined together to represent O; W1, W2 = H.
[8]P1, P2 = H; W1, W2 are combined together to represent O.

Particularly preferred embodiments of the K-252a derivatives are those where the substitutions listed in Table 2 are made.

TABLE 2

| Compound[1] | Y | X | R | $Z^1Z^{2(2)}$ |
|---|---|---|---|---|
| II-2 | H | — | — | O |
| I-4 | H | CO$_2$n-C$_6$H$_{13}$ | OH | O |
| I-6[3] | H | CO$_2$CH$_3$ | OH | O |
| I-10 | NH$_2$ | CH$_2$OH | OH | O |
| I-14 | CH$_3$ | CH$_2$OH | OH | O |
| I-15 | CH$_2$CH$_2$OH | CH$_2$OH | OH | O |
| V[4] | CH$_3$ | — | — | O |
| I-16 | NH$_2$ | CH$_2$NH$_2$.HCl | OH | O |
| I-7 | H | CON(CH$_2$)$_2$OH | OH | H, H |
| VI[5] | CH$_3$ | | | |

[1]R$^1$ and R$^2$ are H except as noted in (3); R$^4$, R$^5$, and R$^6$ are H; R$^3$ is H except as noted in (4).
[2]Z$^1$ and Z$^2$ are both combined to represent oxygen.
[3]R$^1$ and R$^2$ are both Br.
[4]R$^3$ is CH$_2$CH(OH)CH$_2$OH.
[5]R$^3$ and R$^4$ are both CH$_2$CH(OH)CH$_2$OH.

The K-252a derivatives disclosed herein find utility in a variety of settings. For example, in a research environment, the compounds can be utilized to investigate, refine and determine models for "down-stream" effects of autophosphorylation as well as in elucidating the functional activities of the neurotrophins. Autophosphorylation of tyrosine residues of receptor-linked tyrosine kinases (e.g., in trk) is an absolute requirement for the activation of signal transduction pathways which regulate functional responses of, e.g., neurons; accordingly, the disclosed compounds which, e.g., enhance such autophosphorylation, can be used in the development of in vitro assays for analysis of molecular mechanisms impacted by such autophosphorylation. In this way the disclosed compounds can be utilized in the design of improved in vitro models for molecular mechanisms mediated by trk receptor binding to neurotrophins. The utility of the disclosed K-252a derivatives in the design of model systems for the discovery of neurotrophin-like agents is further underscored by the following: (1) the exact mechanism of the neurotrophin signaling pathway is not fully understood; and (2) the association of neurotrophins with trophic and survival-promoting actions of neurons is also not fully understood. Therefore, the disclosed K-252a derivatives can be used, e.g., in the discovery of agents which have marginal neurotrophin like activity in that such agents, when combined with the disclosed K-252a derivatives, can be screened for enhancement of neurotrophin-induced activity.

Degeneration, death or non-functioning of neurons which result in nerve cell degeneration is a feature of many human neurological disorders, including, but not limited to, Alzheimer's; motor neuron disorders (e.g., ALS, Parkinson's); cerebrovascular disorders (e.g., stroke, ischaemia); Huntington's; AIDS dementia; epilepsy; concussive or penetrating injuries of the brain or spinal cord; peripheral neuropathies (e.g., those affecting DRG in chemotherapy-associated peripheral neuropathy); and disorders induced by excitatory amino acids. Because the disclosed K-252a derivatives are useful in enhancing neurotrophin-induced activities of neurotrophin responsive cells (e.g., cholinergic, sensory or DRG neurons), the disclosed compounds beneficially lend themselves to utility as therapeutic agents. Thus, because the disclosed compounds have evidenced utility in, e.g., enhancement of ChAT activity or DRG neuron survival, the utility of the compounds in the treatment of disorders associated with, e.g., decreased ChAT activity or the death of DRG neurons, is within the scope of this disclosure.

Administration of K-252a Functional Derivatives

The compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; for oral administration, particularly in the form of tablets or capsules; or intranasally, particularly in the form of powders, nasal drops, or aerosols.

The composition may be conveniently administered in unit dosage form and may be prepared by any of the methods well known in the pharmaceutical art. See, *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of K-252a derivatives. Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-auryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration.

The materials of this invention can be employed as the sole active agent in a pharmaceutical or can be used in combination with other active ingredients, e.g., neurotrophins, or other factors (i.e., growth factors) or drugs which could facilitate neuronal survival or axonal growth in neurological diseases.

The concentration of a K-252a functional derivative described herein in a therapeutic composition will vary depending upon a number of factors, including the dosage of the K-252a functional derivative to be administered, the chemical characteristics (e.g., hydrophobicity) of the compounds employed, and the route of administration. In general terms, the compounds of this invention may be provided in an aqueous physiological buffer solution containing about 0.1% to 10% w/v compound for parenteral administration. Typical dose ranges are from about 1 µg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the neurological disease, the overall health status of the particular patient, the relative biological efficacy of the K-252a derivative selected, the formulation of the compound excipients, and its route of administration.

The following Examples are presented for elucidation purposes and are not intended to limit the scope of the invention as disclosed.

Example 1: Basal Forebrain Neuron ChAT Assay

Methods: Basal forebrain cultures were prepared from E17 (Embryo Day 17) embryonic rats using trypsin dissociation. Basal forebrains were dissected and collected in hibernation medium consisting of 0.3M $KH_2PO_4$, 20 mM sodium lactate, 195 mM sorbitol, 5 mM glucose, pH 7.4. The tissue was centrifuged for 2 min. at 50×g. After removal of the supernatant, the tissue was resuspended in 1 ml of 0.05% trypsin in calcium-free and magnesium-free Hanks Balanced Salt Solution (CMFHBSS) and 10 mM HEPES, pH 7.2, and incubated for 8 min at 37° C. Bovine serum albumin (BSA) (4%) in HBSS was added and the tube was centrifuged for 2 min. The pellet was resuspended in HBSS buffer containing 10 mM HEPES pH 7.2, 0.5% BSA and DNase. The tissue was mechanically dissociated using fire-polished Pasteur pipers, then passed through a sterile 53 µm Nitex filter and centrifuged through 5 ml of 4% BSA in HBSS. After resuspension of the pellet in culture medium, cells were counted with a hemocytometer. Cells were seeded at $4\times10^5$ cells/cm$^2$ on poly-1-ornithine coated plastic tissue culture 96-well plates in DMEM/F12 medium (50/50 v/v) with 5% horse serum and 0.5% fetal bovine serum. For serum-free conditions, N2 medium containing 0.05% bovine serum albumin (Bottenstein et al., *Proc. Natl. Acad. Sci. U.S.A.*, 76:514–517, 1979) was used. Cells were incubated at 37° C. in a humidified atmosphere of 5% $CO_2$/95% air for 5 days. ChAT activity was measured using a modification of the Fonnum procedure (Fonnum, *J. Neurochem.*, 24:407–409, 1975) according to the improvements of Ishida et al., *J. Neurosci.*, 3:1818–1823 (1983), McManaman et al., *Dev. Biol.*, 125:311–320(1988), and Glicksman et al., *J. Neurochem.*, 61:210–211 (1993). Medium was removed completely from each well, and assay solution containing 0.1M sodium phosphate, pH 7.4, 0.1% NP-40, 0.15M NaCl, 1.5 mM choline chloride, 10 mM EDTA, 0.1 mM eserine sulfate, 3 mCi/ml [$^3$H]acetyl CoA and 100 mM acetyl CoA were added to each well and the plate was incubated at 37° C. for 1.5 hours. Samples were transferred to scintillation vials containing 1.5 ml of 0.1M sodium phosphate buffer, pH 7.4, and 1.5 ml of scintillation cocktail (1.25 g/L tetraphenylboron, 200 ml acetonitrile, 800 ml toluene containing 32 ml/L PPO-POPOP). After vigorous shaking, incorporated radioactivity in the nonaqueous phase was counted using a Packard Scintillation counter (Model 2500TR).

Recombinant rat NT-3 was produced using a recombinant baculovirus expression vector under the control of the polyhedron promoter (Fraser, *In Vitro Cell. and Dev. Biol.*, 25:225–235, 1989). The plasmid (Hallböok et al., *Neuron*, 6:845–858, 1991) pXM-NT3 containing the rat NT-3 cDNA clone was provided by Dr. Ira Black (University of Medicine and Dentistry of New Jersey, Piscataway, N.J.). NT-3 cDNA was subcloned into transfer vector pVL1392 (obtained from InVitrogen Corp., San Diego, Calif.) for recombinant virus production. Recombinant baculovirus was produced by cotransfecting *Spodoptera frugiperda* insect cells (Sf-21) in monolayer with 1 µg of *Autographa californica* nuclear polyhidrosis virus DNA (InVitrogen or Baculogold™ by PharMingen, San Diego, Calif.) and 2–4 µg of the transfer vector by the calcium phosphate method of Smith et al., *J. Virol.*, 46:584–593 (1983). Recombinant plaques were verified as being recombinant by the hybridization of [$^{32}$P] labeled NT-3 sequences to blots of infected cell lysates (Summers and Smith, in *A Manual of Methods for Baculovirus Vectors and Insect Cell Culture Procedures*, pp. 29–32, 1987). The recombinant virus was plaque-purified and amplified. The insect cell lines, *Trichoplusia ni* Tn-5B1-4 (InVitrogen Corp.), were infected with recombinant baculovirus with a multiplicity of infection of 2 in 0.2 ml/cm$^2$ of Ex-Cell 401 (JRH Biosciences, Lenexa, Kans.). The conditioned medium containing NT-3 was harvested at 4 days postinfection. Approximately 1 liter of conditioned medium containing the NT-3 was centrifuged at 25,000×g for 15 min. The supernatant was then passed through a 1 cm×4 cm carboxymethyl-Sepharose Fast Flow column (Pharmacia, Piscataway, N.J.). After washing with column buffer (150 mM NaCl, 100 mM sodium phosphate pH 6.2), with 250 mM NaCl, in 100 mM Tris●HCl, pH 7.6, it was then eluted with 500 mM NaCl in 100 mM Tris●HCl, pH 7.6. NT-3-containing fractions were identified by sodium dodecyl sulfate polyacrylamide gel electrophoresis (Laemmli, *Nature,* 277:680–685, 1970) followed by silver staining to detect protein by the method of Morrissey, *Anal. Biochem.,* 117:307–310 (1981) and pooled. These were then applied to a 4.6×250 mm Vydac reverse phase C4 column using a Rainin HPLC operating system. Following washing with both 0.1% trifluoacetic acid (TFA) and 5% (v/v) acetonitrile/0.1% TFA, NT-3 was eluted using a linear gradient of 5–65% acetonitrile in 0.1% TFA. NT-3-containing fractions were dried under vacuum in a Speed-Vac (Savant, Farmingdale, N.Y.) without heating. NT-3 was resuspended in 10 mM acetic acid with 0.1% BSA and stored in aliquots at –70° C.

Example 1A: ChAT Activity Mediated by NT-3

Neurotrophic activity of NT-3 was assayed by determining the choline acetyltransferase (ChAT) activity in basal forebrain cultures, following the methodology described above. NT-3 was added at the indicated concentrations after cells were plated for 2 hours to allow attachment to substrate. ChAT activity was measured after 5 days in vitro. NT-3 resulted in a dose dependent increase in ChAT activity in basal forebrain cultures with a maximum efficacy (1.5 to 2-fold increase) at 1000 ng/ml (FIG. 1). In serum-free media, NT-3 was more efficacious (2 to 2.5-fold increase) at 1000 ng/ml (FIG. 1).

Example 1B: Enhancement of Neurotrophin Induced Activity of NT-3 Using K-252a Derivative I-16

Figure 2:
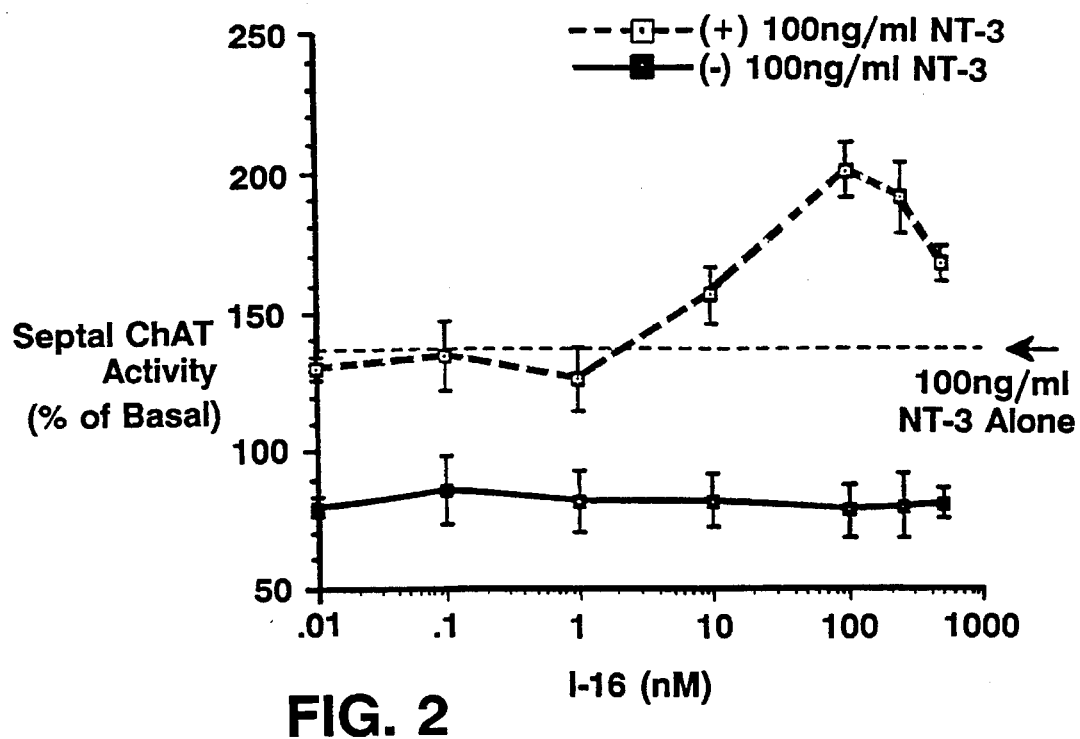
FIG. 2 is a graph which depicts the dosage effect of a representative K-252a functional derivative (I-16) and NT-3 on ChAT activity in embryonic rat basal forebrain cultures.

The ability of K-252a derivative I-16 to enhance NT-3 activity in basal forebrain cultures was determined using ChAT activity as a measure of cholinergic neuron function or survival. I-16 alone had no effect on ChAT activity. However, I-16 in the presence of NT-3, gave a dose dependent enhancement of ChAT activity (FIG. 2) to levels greater than those elicited by NT-3 alone. The results shown are the result of a single application of NT-3 and I-16 on the day of culture initiation, indicating a prolonged effect on the survival or function of basal forebrain cholinergic neurons. Methods were as detailed in Example 1.

Example 1C: Enhancement of Neurotrophin Induced Activity of NT-3 Using Different K-252a Derivatives Functional derivatives of K-252a were tested in the basal forebrain ChAT assay for their ability to potentiate NT-3 activity. The data in Tables 3A and 3B show that K-252a derivatives resulted in significant enhancement of NT-3 activity at one or more of the concentrations tested. Twenty-four of these derivatives show activity at 10 nM NT-3. In the presence or absence of serum, the listed compounds enhanced ChAT activity over the ChAT activity elicited by NT-3 alone. The listed derivatives had no effect on ChAT activity in the absence of NT-3. Our data show the result of a single application of NT-3 and the listed derivative on the day of culture initiation, indicating a prolonged effect on the survival or function of basal forebrain cholinergic neurons. Methods were as detailed in Example 1.

TABLE 3A

| Compound | ChAT Activity (% NT3) Basal Forebrain Cultures | | |
|---|---|---|---|
| | 10 nM | 100 nM | 300 nM |
| IV | inactive | 115 | 131 |
| II-2 | inactive | inactive | 139 |
| I-1 | 172 | 136 | toxic |
| I-2 | 138 | 142 | 108 |
| I-3 | 135 | 148 | 130 |
| I-4 | 120 | 149 | 146 |
| I-5 | 115 | 150 | 150 |
| I-6 | 146 | 183 | 183 |

TABLE 3A-continued

| Compound | ChAT Activity (% NT3) Basal Forebrain Cultures | | |
|---|---|---|---|
| | 10 nM | 100 nM | 300 nM |
| III-1 | 120 | 120 | 119 |
| I-7 | 121 | inactive | toxic |
| I-8 | 118 | 132 | 120 |
| I-9 | 128 | 160 | 172 |
| I-10 | 120 | 188 | 185 |
| I-11 | 163 | inactive | inactive |
| I-12 | 153 | inactive | inactive |
| I-13 | 172 | 141 | toxic |
| I-14 | 155 | 181 | 181 |
| I-15 | 159 | 177 | 176 |
| V | inactive | 142 | 148 |
| VI | inactive | 130 | 129 |
| I-16 | 143 | 196 | 206 |
| II-5 | inactive | 122 | 151 |
| I-17 | 154 | 176 | 127 |
| I-18 | inactive | 123 | 149 |
| I-19 | inactive | 113 | 116 |
| I-20 | 112 | 128 | 127 |
| I-21 | 165 | 143 | inactive |
| III-2 | 159 | 181 | 177 |

TABLE 3B

| Compounds | ChAT Activity (% of NT-3) Basal Forebrain Cultures | |
|---|---|---|
| | 10 nM | 100 nM |
| I-23 | inactive | 128 |
| I-22 | 150 | inactive |
| I-24 | 125 | 165 |
| I-25 | 125 | 164 |

Example 2: DRG Neuron Survival Assay

Methods: Dorsal root ganglia were dissected from embryonic age day 9 chick embryos (stage 35) and dissociated cells prepared by subsequent Dispase (neutral protease, Collaborative Research) treatment. Neurons were seeded at low density (1.8×10$^4$ cells/cm$^2$) into 96-well poly-1-ornithine and laminin coated plates. Cells were cultured for 48 hours in serum-free N$_2$ medium containing 0.05% bovine serum albumin (Bottenstein et al., *Proc. Natl. Acad. Sci. U.S.A.,* 76:541–517, 1979) at 37° C. in a humidified atmosphere, 5%CO$_2$/95% air. Cell survival was assessed at 48 hours using a calcein viable fluorimetric assay. Calcein AM was diluted 2× in Dulbecco's phosphate buffered saline (DPBS) to 2× the final assay concentration (6M), and 100 μl of the diluted calcein AM was added to culture wells containing 100 μl of medium. The plates were then incubated for 1 hour at 37° C. Cells were then washed 4 times with PBS to remove excess calcein not taken up by cells. The plate was read using a Millipore plate reading fluorimeter (Cytofluor 2350) at emission=485 nm and excitation= 538 nm. After subtraction of blank values (wells containing medium but no cells), relative fluorescent values reflect a quantitative measurement of cell survival in the predominantly (>95%) neuronal cultures (Bozyczko-Coyne et al., *J. Neuroscience Methods,* 50:205–216, 1993).

Example 2A: DRG Neuron Survival Mediated by NT-3

The effect of NT-3 on neuronal survival was assayed in dorsal root ganglion neuron cell cultures. Cell survival was measured by uptake of calcein AM (Molecular Probes, Eugene, Oreg.), an analog of the dye fluorescein diacetate. Calcein is taken up by cells and cleaved intracellularly by live cells to fluorescent salts that are retained by intact membranes of viable cells. Microscopic counts of viable neurons correlated directly with relative fluorescence values obtained using the fluorimetric viability assay method, described in Example 2. This method provides a reliable and quantitative measurement of cell survival. Dorsal root ganglion neuron survival was enhanced by NT-3 in a dose-dependent manner, with a maximal 1.6-fold over control at 50 ng/ml NT-3. Methods were as described in Example 2.

Example 2B: Enhancement of Neurotrophin Induced Activity of NT-3 Using K-252a Derivative I-16

Figure 3:
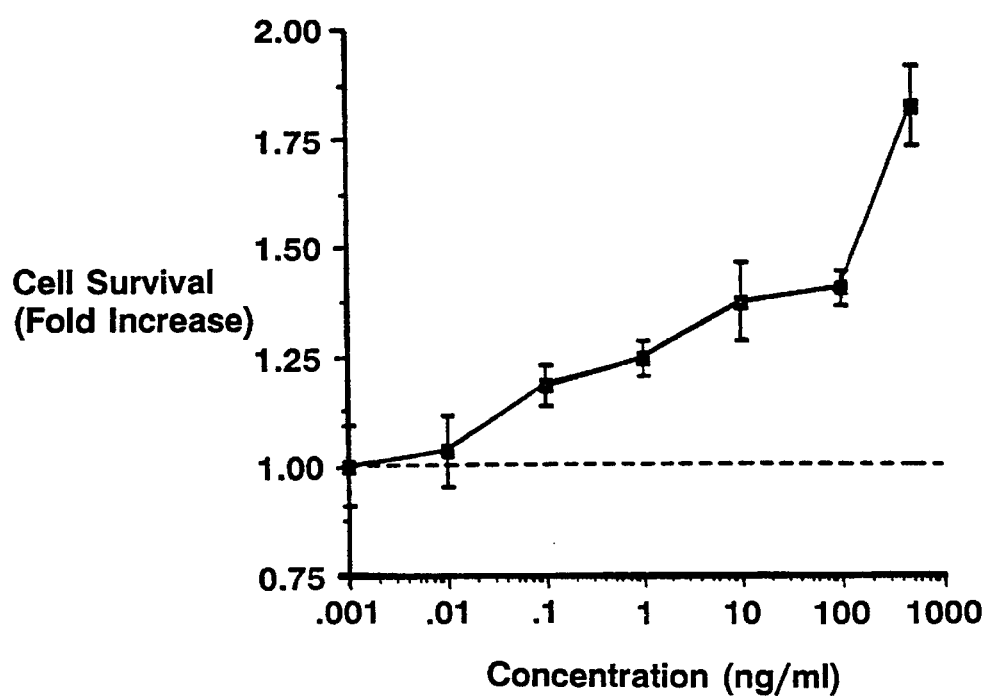
FIG. 3 is a graph illustrating the dosage effect of NT-3 on dorsal root ganglion neuron survival in vitro.
Figure 4:
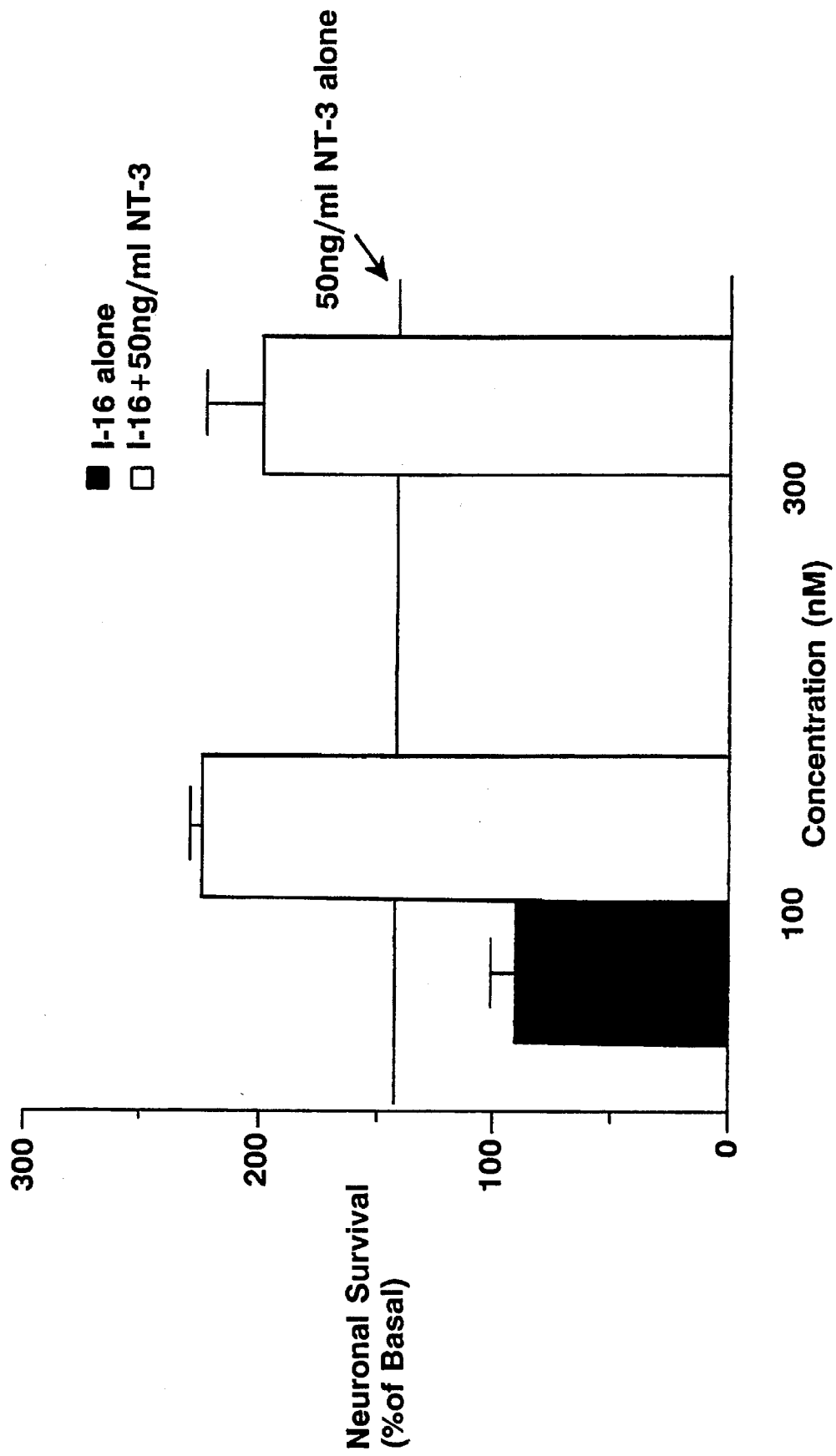
FIG. 4 is a graph illustrating the effect of NT-3 and a representative K-252a functional derivative (I-16) on dorsal root ganglion neuron survival in vitro.

In the absence of K-252a derivative I-16, NT-3 elicited a 40% increase in DRG cell survival over untreated control cultures (FIG. 3). In the presence of 100 or 300 nM of I-16, there was a marked enhancement of the ability of NT-3 to promote DRG survival to values greater than 200% of untreated control cultures. In the absence of NT-3, I-16 had no effect on the survival of DRG neurons. Methods were as described in Example 2.

Example 2C: Enhancement of Neurotrophin Induced Activity of NT-3 Using Different K-252a Derivatives Several different K-252a functional derivatives were tested in the DRG neuronal survival assay for ability to enhance NT-3 activity. Derivatives tested at 100 nM resulted in significant enhancement of NT-3 activity. Compounds listed in Table 4 enhanced neuronal survival beyond the increase induced by NT-3 alone. The results shown are the result of a single application of NT-3 and the listed compounds on the day of culture initiation, indicating a prolonged effect on neuronal survival. Methods were as described in Example 2.

TABLE 4

| Compound | DRG Neuronal Survival (% NT3) 100 nM |
| --- | --- |
| II-2 | 162 |
| I-4 | 134 |
| I-6 | 174 |
| I-10 | 178 |
| I-14 | 159 |
| I-15 | 182 |
| V | 148 |
| I-16 | 154 |

Example 3: PC-12 trk Tyrosine Phosphorylation Assay

Methods: PC-12 cells (obtained from American Type Culture Collection) were maintained in Dulbecco's Modified Eagle's Medium (DMEM) containing 2 mM glutamine, 7.5% horse serum, 7.5% fetal bovine serum, 1 mM sodium pyruvate and penicillin and streptomycin. Cells were incubated at 37° C. in a humidified atmosphere of 5% $CO_2$/95% air. Subconfluent cell monolayers were incubated at 37° C. for 2 hours in serum-free DMEM containing vehicle or a K-252a functional derivative. Where indicated, NT-3 (50 ng/ml) was added at 37° C. for 5 minutes. All samples including controls were exposed to 0.075% DMSO. To end the experiment, cells were rinsed with ice-cold phosphate-buffered saline (PBS) followed by lysis in RIPA buffer (1% Triton X-100, 1% sodium deoxycholate, 0.1% sodium dodecylsulfate, 150 mM sodium chloride, 10 mM Tris, pH 7.5, containing 20 ug/ml aprotinin, 1 mM phenylmethylsulfonyl fluoride (PMSF), 10 μM leupeptin and 1 mM sodium vanadate). Lysates were passed through a 26 gauge needle to shear DNA followed by a 15 minute centrifugation at 14,000×g. Supernatants were normalized to protein concentration. Pananti-trk antibody (which recognizes trk A, trk B and trk C), was added to lysates, and after a 2 hour incubation at 4° C., the immune complex was collected on Protein A-Sepharose beads. Proteins were eluted from the beads with 4X Laemmli buffer (Laemmli, Nature, 277:680–685, 1970) separated by sodium dodecyl sulfate polyacrylamide gel electrophoresis and transferred to PVDF membrane. The membrane was probed with anti-phosphotyrosine antibody (UBI). Antibody binding was visualized by enhanced chemiluminescence (ECL Kit, Amersham, Inc.).

Figure 5:
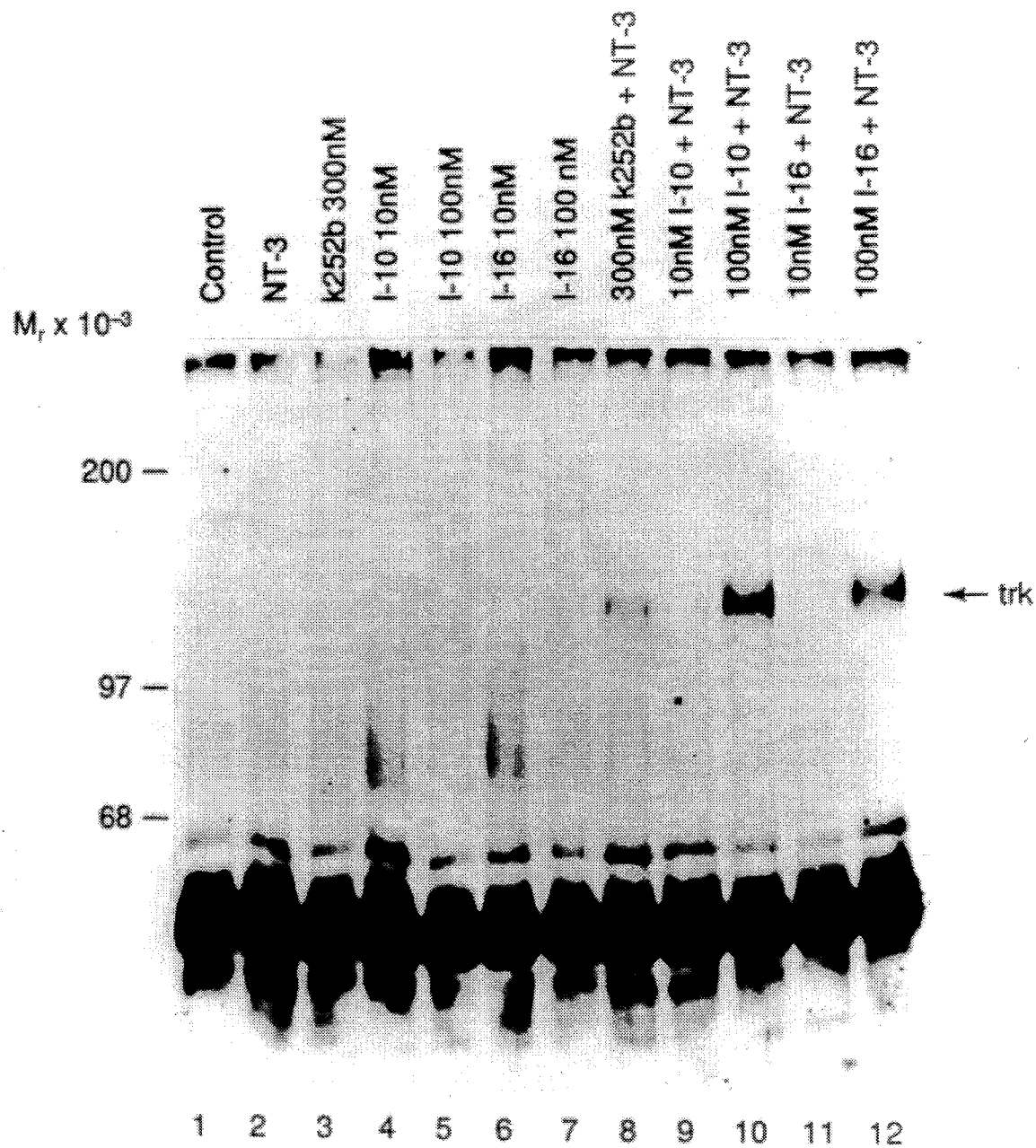
FIG. 5 is an immunoblot showing enhanced tyrosine phosphorylation of the trk cell receptor when PC-12 cells are contacted by a K-252a functional derivative.

Example 3A: Enhancement of Neurotrophin Induced Activity of NT-3 Using Different K-252a Derivatives Pheochromocytoma (PC-12) cells were incubated for 2 hours with vehicle (<0.1% DMSO) or a K-252a functional derivative. Cells were then incubated for 5 minutes in the absence or presence of NT-3. Cells were lysed and immunoprecipitated with pan-anti-trk antibody. Proteins were separated by sodium dodecyl sulfate (SDS) polyacrylamide gel electrophoresis and transferred to polyvinylidene difluoride (PVDF) membrane. The membrane was immunoblotted with anti-phosphotyrosine antibody to allow visualization of tyrosine phosphorylated trk. No autophosphorylation of trk was observed in untreated cells (FIG. 5, lane 1). In the absence of any K-252a functional derivative, NT-3 did not elicit detectable tyrosine phosphorylation of trk (lane 2). Similarly, in the absence of NT-3, neither K-252b at 300 nM (lane 3) nor compounds I-16 or I-10 at 10 and 100 nM (lanes 4–7) caused autophosphorylation of trk. In combination, however, NT-3+300 nM K-252b (lane 8), or 100 nM compound I-10 (lane 10) or 100 nM compound I-16 (lane 12) resulted in a striking tyrosine phosphorylation of trk. Incubation of NT-3 with 10 nM compound 1–10 or compound I-16 (lanes 9 and 11) yielded smaller but measurable increases in trk tyrosine phosphorylation.

Example 4: trk Receptor-Specific Mitogenic Assay

Methods: Clonal NIH-3T3 cells (ATCC Accession Number CRL1658), which separately overexpress rat trk A, trk B and trk C, were generated by transfection and selection. Blunt-ended cDNA for trk A (Genebank Accession Number L14445; see Valenzuela, D. M. et al 10 Neuro. 1, 1993); trk B (Genebank Accession Number L14446; see Valenzuela, supra) and trk C (Genebank Accession Number L03813; see Merlio, J. P. et al 51 Neuro. 513, 1992) were separately inserted within the Eco RI site (bp 1215) of the vector pMEX-neo (See Kho, C. J. and Zarbl, H., 89 PNAS 2200, 1992, for a description of pMEX-neo). Rat cDNA for trk C is further available under Genebank Accession Number L14447; see Valenzuela, supra. Transfection protocols, as generally described in Molecular Cloning, J. Sambrook, E. F. Fritsch & T. Maniatis, Cold Spring Harbor Laboratory Press, 1989, were followed for transfection of the NIH-3T3 cells by the pMEX-neo:trk A, pMEX-neo:trk B; and pMEX-neo:trk C vectors. The transfected cell lines were utilized for determination of mitogenesis as mediated by the binding of neurotrophins to specific trk receptors.

The following protocol was used for the mitogenesis assay: NIH-3T3 cells transfected with the specified vectors were plated in a 96 well format at a concentration of $1 \times 10^4$ cells/well in 100 μl of N2 medium (Bottenstein, supra) containing 0.05% bovine serum albumin for 24 hrs. Thereafter, the medium was removed and replaced with 50 μl of N2 medium containing the designated K-252a derivatives at the designated concentrations (0.1 nM; 1.0 nM; 10 nM; and 100 nM) (0.025% DMSO final concentration in each well) in the presence of previously determined maximal response concentrations of the specified neurotrophins (total volume in each well: 50 μl), followed by the addition of 1.5 μCi of $^3$H-thymidine/well for 24 hrs. Thereafter, cells were harvested in PBS onto glass filter fibers with the Brandel apparatus (model no. MB-48R), lysed and fixed with 10% trichloroacetic acid, followed by rinsing with PBS. The filters were then removed and placed in 4 ml Ecosafe Scintillant (Research Products Int. Cat. No. 111195) for counting (Packard model no. Tri-Carb 2500TR) incorporation of labeled tritium.

Example 4A: Enhancement of Neurotrophin Induced Activity of NT-3 Using Different K-252a Derivatives Following the methodology described above, various concentrations of the designated K-252a derivatives were analyzed to determine the enhancement of mitogenesis mediated by the binding of NT-3 to trk A using the pMEX-neo:trk A cell line; as noted previously, the preferred trk A-ligand is NGF, not NT-3.

Previously determined maximal response concentrations, relative to untreated cells, were determined to be as follows: for NGF binding to trk A, 0.1 ng/ml NGF provided a 7.1-fold increase in mitogenesis (as measured by incorporation of tritium labelled thymidine in the lysed cells) compared to untreated controls; thus, for trk A, the maximal response (as defined by the preferred ligand for trk A, NGF) was 7.1. For NT-3 binding to trk A, concentrations of between 500 ng/ml and 1000 ng/ml were required to achieve the maximal response observed with NGF binding (data not shown).

For these analyses, the concentration of NT-3 was maintained at 100 ng/ml. Results are presented in Table 5; values presented are for the fold-increase in mitogenesis compared to untreated controls. A value above 1.5 was arbitrarily defined as an enhancement of the mitogenesis by NT-3 binding of trk A in the presence of the designated K-252a derivative. K-252a, which does not have a positive effect in the mitogenesis assay, was used as a control. The term "NT" indicates "not tested."

TABLE 5

| Compound/ Derivative | Mitogenic Assay Concentration of Compound/Derivative | | | |
|---|---|---|---|---|
| | 0.1 nM | 1.0 nM | 10 nM | 100 nM |
| K-252a | 1.0 | 1.4 | 1.4 | 0.6 |
| II-5 | 1.3 | 1.5 | 1.6 | 3.2 |
| I-7 | 1.7 | 2.9 | 4.4 | 4.4 |
| I-16 | 2.9 | 4.3 | 3.7 | 5.0 |
| I-15 | 4.1 | 4.1 | 5.3 | 4.9 |
| I-6 | 3.2 | 4.3 | 3.1 | 0.9 |
| I-14 | 1.9 | 5.0 | 7.4 | 5.2 |
| V | NT | NT | 3.4 | 6.0 |
| VI | NT | NT | 1.9 | 7.1 |

Synthesis of K-252a Functional Derivatives

The chemical synthesis of representative K-252a derivatives is outlined below. Additional derivatives of K-252a may be prepared de novo by chemical synthesis using methods known to those skilled in the art. For example, procedures used for preparation of the compound represented in Formula I are described by Murakata et al., U.S. Pat. Nos. 4,923,986 and 4,877,776 hereby incorporated by reference. Procedures used for the preparation of the compound represented in Formula II are described by Moody et al., *J. Org. Chem.*, 57:2105–2114, 1992, Steglich et al., Angew. Chem. Int. Ed. Engl., 459–460, 1980, Nakanishi et al., *J. Antobiotics*, 39:1066–1071, 1986, and Published Japanese Patent Application Numbers 60-295173, 62-327858, 62-327859 and 60-257652.

Chemical Synthesis and Analysis of Representative K-252a Derivatives

Compound numbers refer to K-252a derivatives listed in Table 1.

Preparation of Compound IV

POCl$_3$ (0.28 ml, 3 mmol) and Compound (A) (311 mg, 1 mmol) were added to 20 ml of dimethylformamide under ice cooling, followed by stirring at 90° C. for 4 hours. The precipitates were collected by filtration, and washed successively with water and methanol to give 250 mg (yield 74% of Compound IV.

The starting material compound (A) has been described (Nakanishi et al., *J. Antibiotics*, 39:1066–1071, 1986).

The following characteristic values may be obtained by nuclear magnetic resonance spectroscopy (NMR) or mass spectroscopy (MS):

$^1$H-NMR (DMSO-d$_6$) δ (ppm)(: 5.298(2H, s), 7.255–8.073(7H, m), 9.036(1H, d, J=7.7 Hz), 9.300(1H, s), 11.891(1H, s) 12.175(1H, s)

EI-MS (m/z ): 339 (M)$^+$

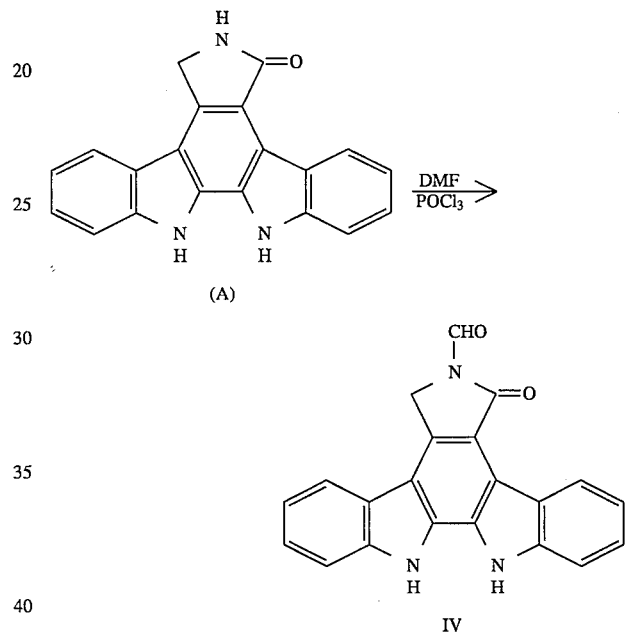

Preparation of Compound V

Compound (B) (208 mg, 0.61 mmol) was dissolved in 20 ml of tetrahydrofuran, and then 74 mg (1.83 mmol) of sodium hydride (60%) was added thereto, followed by stirring at room temperature for 10 minutes. Allyl bromide (0.063 ml, 0.73 mmol) was added thereto and the mixture was stirred at room temperature for 15 hours. To the solution was added a saturated aqueous solution of ammonium chloride, and the organic layer was washed with a saline solution and dried over magnesium sulfate. After evaporation of the solvent, the residue was subjected to silica gel column chromatography (chloroform) to give 135 mg (yield 58%) of Compound (C).

The following characteristic values for Compound C may be obtained by NMR:

$^1$H-NMR (CDCl$_3$+DMSO-d$_6$; 4/1) δ (ppm): 3.04(3H, s), 4.80–5.20(4H, m), 5.96–6.40(1H, m), 7.28–7.72(6H, m), 9.18(1H, d, J=8.0 Hz), 9.20(1H, d, J=8.0 Hz), 9.84(1H, s)

Compound (C) (145 mg, 0.38 mmol) was dissolved in a mixture of 7 ml of tetrahydrofuran and 0.5 ml of pyridine, and then 4 ml of tetrahydrofuran containing 200 mg of osmium tetroxide was added thereto, followed by stirring at room temperature for 6 hours. Sodium thiosulfate (348 mg), 7 ml of water, and 7 ml of pyridine were added to the reaction solution, followed by stirring at room temperature for 1 hour. To the solution was added tetrahydrofuran for dilution, and the mixture was washed with a saturated aqueous solution of sodium bicarbonate, and dried over magnesium sulfate. After evaporation of the solvent, the residue was subjected to silica gel column chromatography chloroform/methanol=97/3) to give 93 mg of Compound II-3.

The starting material Compound (B) has been described by Gribble and Berthel, *Tetrahedron*, 48:8869 (1992).

The following characteristic values may be obtained by NMR and MS:

$^1$H-NMR (DMSO-$d_6$) δ (ppm): 3.186 (3H, s), 3.633 (2H, m), 4.068(1H, brs), 4.804(1H, dd, J=7.9, 15.6 Hz), 4.955(1H, dd, J=3.2 15.6 Hz), 5.407(1H, d, J=4.9 Hz), 5.480 (1H, t, J=5.1 Hz), 7.351–7.818 (6H, m), 9.093(1H, d, J=7.9 Hz), 9.131(1H, dd, J=0.5, 7.9 Hz), 11.736(1H, s)

FAB-MS (m/z): 414 (M+1)$^+$.

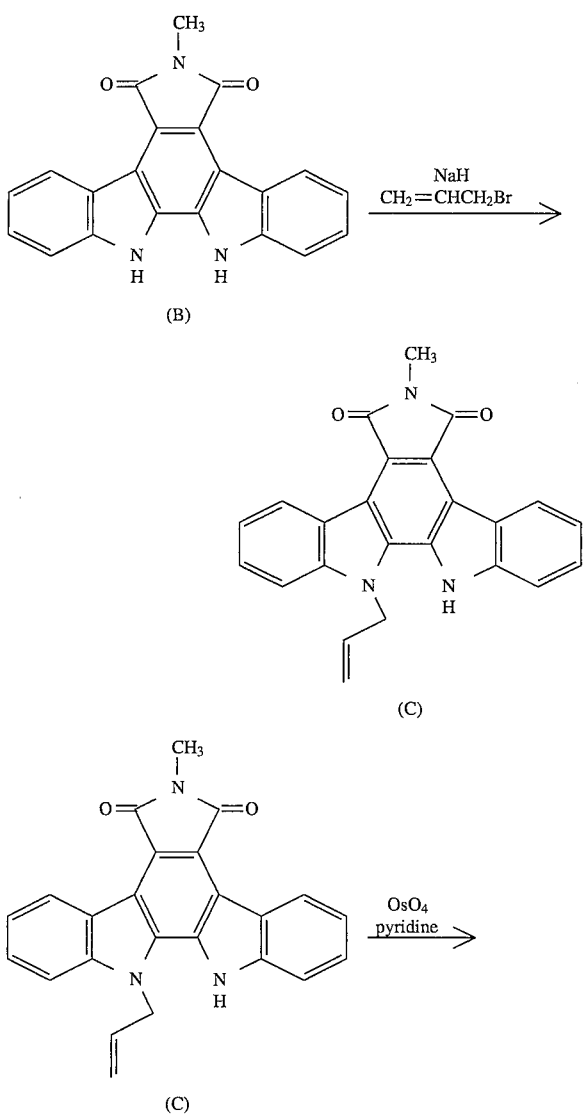

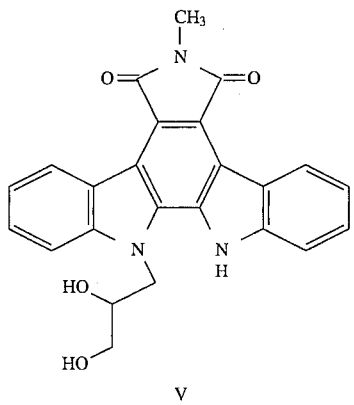

Preparation of Compound VI

Compound (D) can be prepared by reaction of Compound (B) with 2 to 4 equivalents of allyl bromide in the presence of 3 to 5 equivalents of a base. An example of the base is an alkali metal hydride such as sodium hydride. As a reaction solvent, tetrahydrofuran, dimethylformamide, or the like is used. The reaction is completed in 0.5 to 15 hours at −10 to 40° C.

Compound VI can be obtained by treatment of Compound (D) with 2 to 4 equivalents of an oxidant. An example of the oxidant is OsO$_4$. As a reaction solvent, a mixed solvent of tetrahydrofuran and pyridine or the like is used. The ratio of tetrahydrofuran to pyridine is 1/20 to 1/5. The reaction is completed in 3 to 8 hours at 0 to 40° C.

The following characteristic values for Compound (D) may be obtained by using NMR and MS:

$^1$H-NMR (CDCl$_3$) δ (ppm): 3.21(3H, s), 4.92–6.40(10H, m), 7.40–7.64 (6H, m), 9.32 (2H, d, J=8.0 Hz)

EI-MS (m/z): 419 (M)$^+$

The following characteristic values for Compound (II-4) may be obtained by using NMR and MS:

$^1$H-NMR (DMSO-$d_6$) δ (ppm): 2.965 (2H, t, J=5.5 Hz), 3.139 (2H, m), 3.196(1.5H, s), 3.198(1.5 H, s), 3.626 (2H, m), 4.651–4.945 (4H, m), 7.399 (2H, t, J=7.2 Hz), 7.612 (2H, dt, J=1.2, 7.2 Hz), 7.828 FIG. 8 (2H, t, J=8.7 Hz), 9.142 (2H, d, J=7.9 Hz)

FAB-MS (m/z) :488 (M+1)$^+$

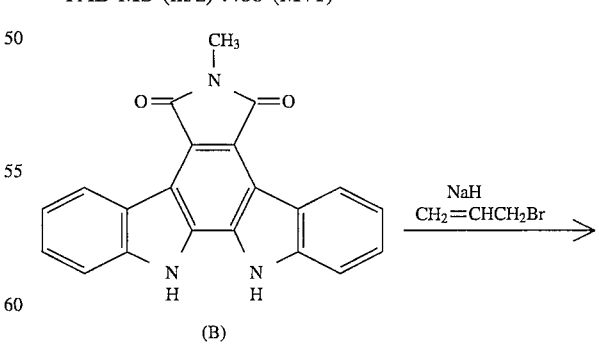

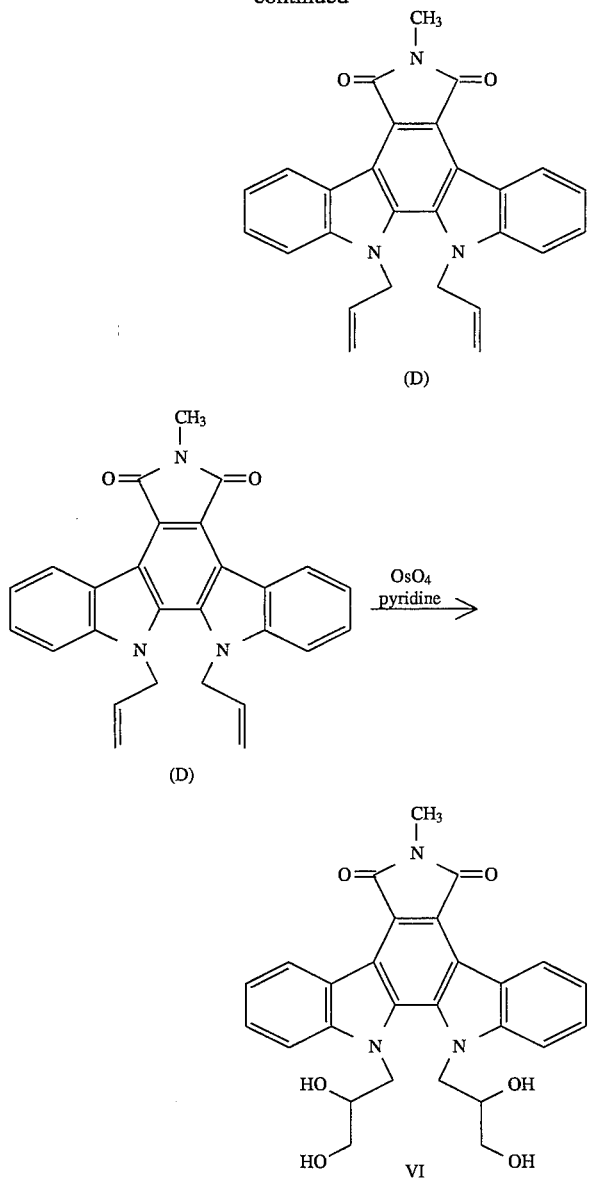

Preparation of Compounds I-9 and I-14

Figure 6:
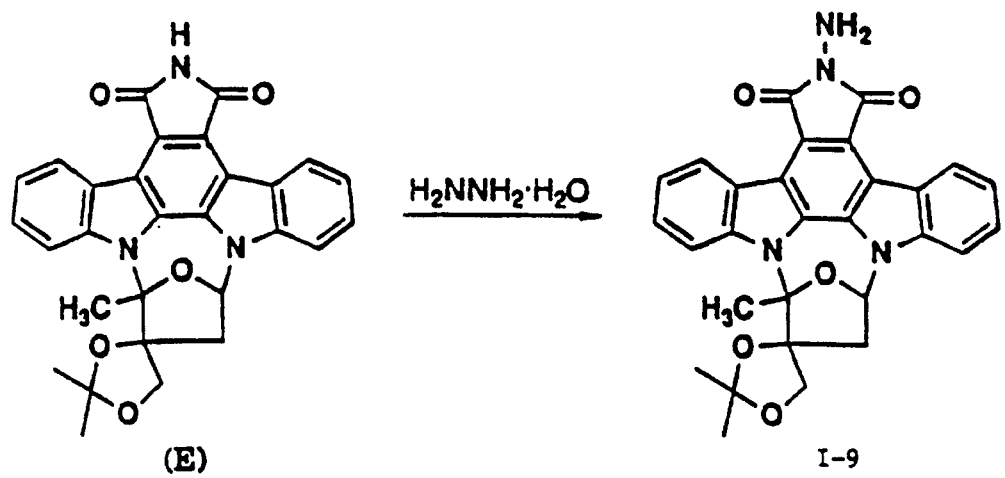
FIG. 6 is a figure outlining the chemical synthesis of compounds I-9 and 1-14.
Figure 6:
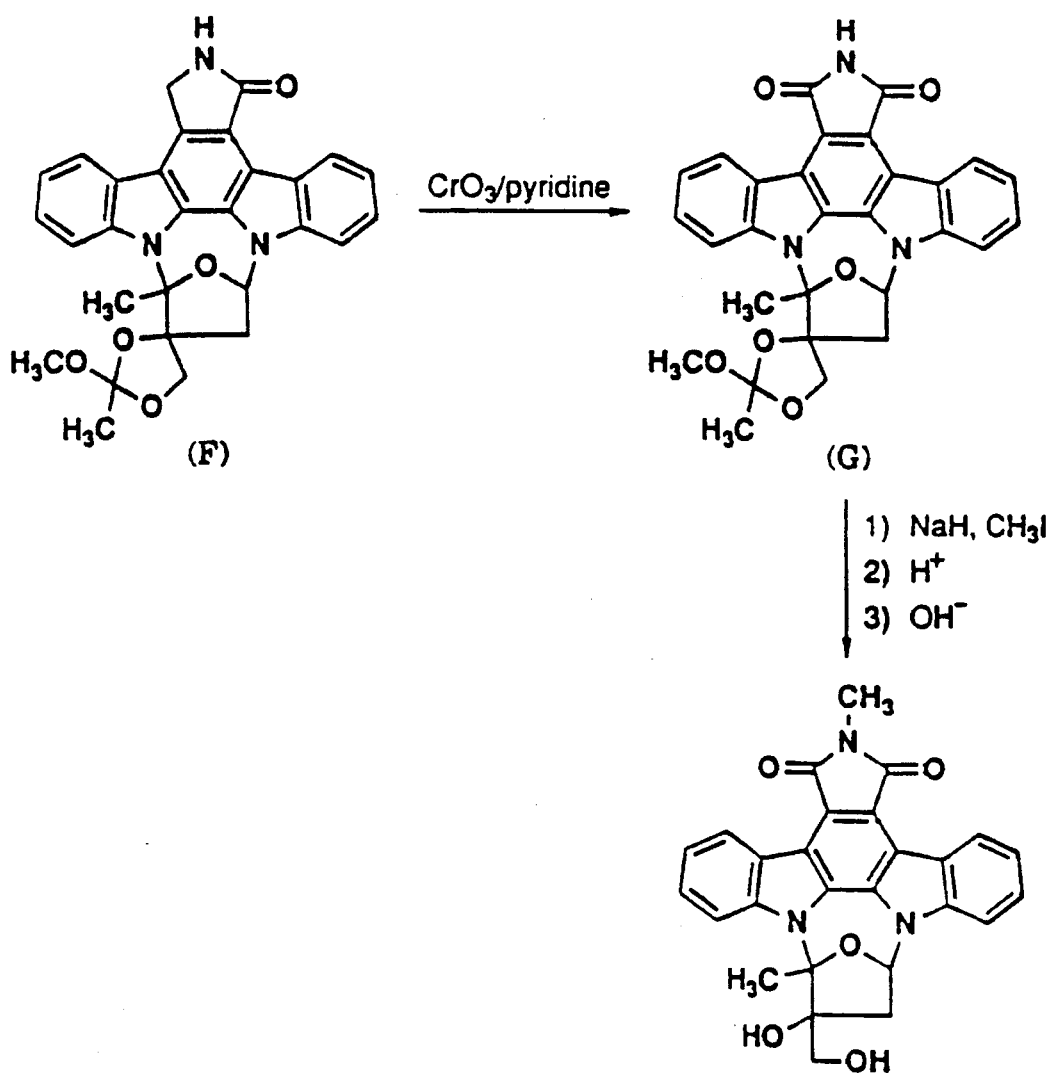
Figure 7:
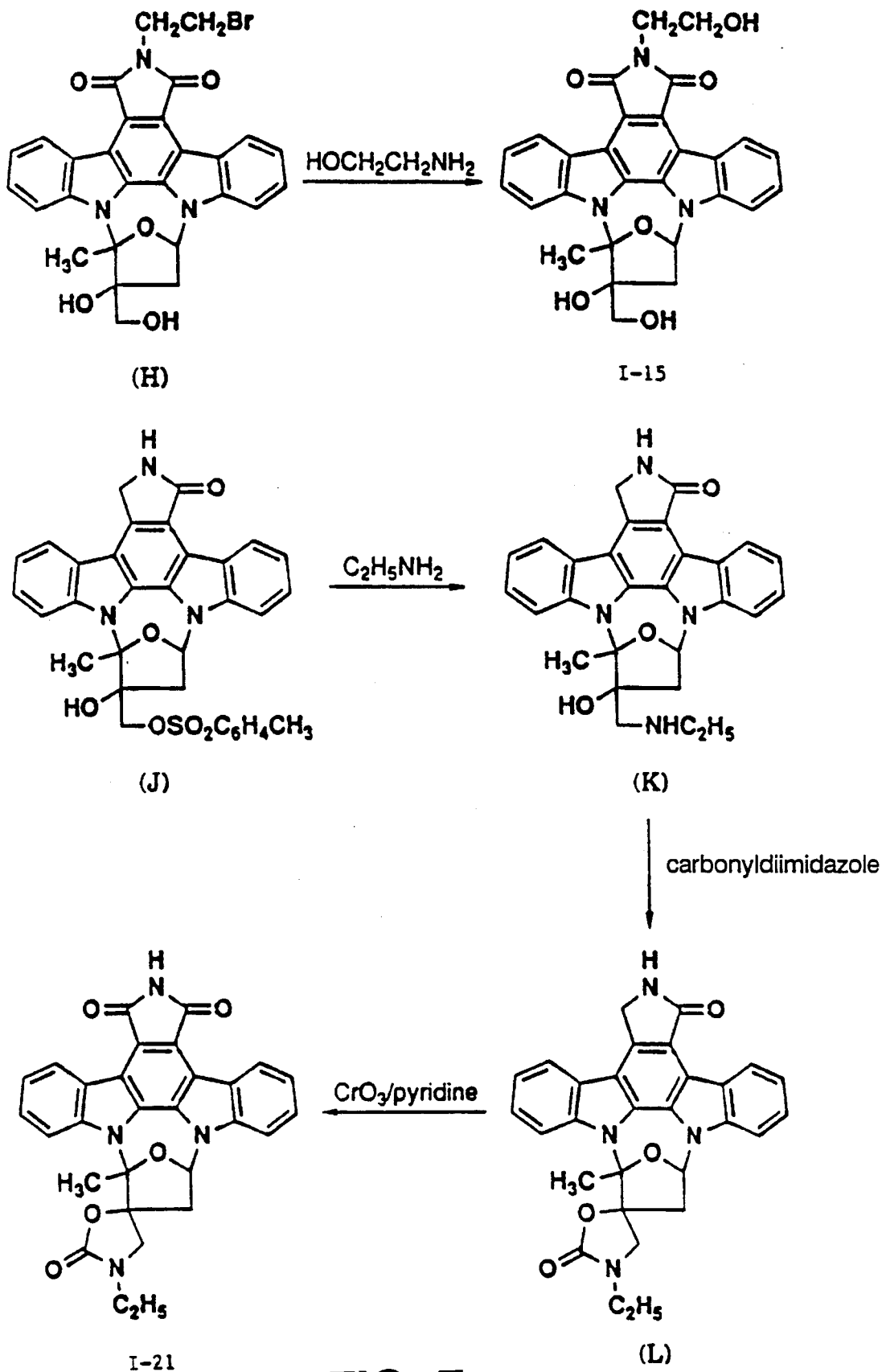
FIG. 7 is a figure outlining the chemical synthesis of compounds 1-15 and 1-21.

Compound (E) (see FIG. 6 and Japanese published Unexamined Patent Application No. 295589/88) (49.3 mg, 0.1 mmol) was dissolved in 3 ml of dioxane, and then 0.1 ml of hydrazine hydrate was added thereto, followed by stirring at 110° C. for 2 hours. After evaporation of the solvent, methanol was added to the residue and the precipitates were collected by filtration to give 40 mg of Compound I-9.

$^1$H-NMR (CDCl$_3$) δ (ppm): 1.19(3H, s), 1.36(3H, s), 2.30(3H, s), 2.45(1H, dd, J=5.0, 14.0 Hz), 2.91(1H, dd, J=7.0, 14.0 Hz), 4.10(1H, d, J=10.0 Hz), 4.54(1H, d, J=10.0 Hz), 6.63(1H, dd, J=5.0, 7.0 Hz), 7.22–7.86 (6H, m), 8.97(1H, d, J=8.0 Hz), 9.25(1H, d, J=8.0 Hz)

SIMS (m/z): 509 (M+1)$^+$

Chromic acid (2.8 g, 28 mmol) was added to 20 ml of pyridine under ice cooling, and then 5 ml of pyridine containing 1.98 g (4 mmol) of Compound (F) (see FIG. 6 and Japanese Published Unexamined Patent Application No. 295589/88) was added thereto, followed by stirring at room temperature for 12 hours. After the solution was filtered through Celite, the solvent was evaporated, and the residue was subjected to silica gel column chromatography (chloroform) to give 0.98 g (Yield 48%) of Compound (G) see FIG. 6.

The following characteristic values for Compound (G) may be obtained by using NMR:

$^1$H-NMR (CDCl$_3$) δ (ppm): 1.52 (2.1H, s), 1.60 (0.9H, s), 2.32 (0.9H, s), 2.36 (2.1H, s), 2.67(1H, dd, J=5.0, 14.0 Hz), 3.09 (2.1H, s), 3.38 (0.9H, s), 4.72–4.81 (2H, m), 6.72(1H, m), 7.20–9.32 (8H, m)

Compound (G) (305 mg, 0.6 mmol) was dissolved in 6 ml of dimethylformamide, and then 36 mg (0.9 mmol) of sodium hydride (60%) was added thereto under ice cooling, followed by stirring at the same temperature for 10 minutes. Methyl iodide ( 0.056 ml, 0.9 mmol ) was added thereto and the mixture was stirred at the same temperature for 30 minutes. A saturated aqueous solution of ammonium chloride (1 ml) and 10 ml of water were added to the solution and the precipitates were collected by filtration.

The product thus obtained was dissolved in a mixture of 25 ml of chloroform, 1 ml of methanol, and 1 ml of 3N HCl, and the solution was stirred at 60° C. for 10 minutes. The solution was washed with a saturated aqueous solution of sodium bicarbonate, and then 10 ml of tetrahydrofuran, 10 ml of methanol, and 1.5 ml of 2N NaOH were added to the organic layer, followed by stirring at room temperature for 10 minutes and evaporation of the solvent. After chloroform was added thereto for dilution, the mixture was washed successively with a 5% aqueous solution of citric acid and a saline solution, and dried over magnesium sulfate. After evaporation of the solvent, the residue was subjected to silica gel column chromatography (chloroform/methanol= 98/2) to give 102 mg (yield 36%) of Compound I-14. The following characteristic values for Compound I-14 may be obtained by using NMR and MS:

$^1$H-NMR (CDCl$_3$+DMSO-d$_6$' 41) δ (ppm): 2.24(3H, s), 3.18(3H, s), 4.81(1H, t, J=6.0 Hz), 6.83(1H, dd, J=5.0, 7.0 Hz), 7.24–8.08 (6H, m), 9.06(1H, d, J=7.0 Hz), 9.25(1H, d, J=7.0 Hz)

EI-MS (m/z) :467 (M+1)$^+$

Preparation of Compounds I-15 and I-21

Compound (H) (see FIG. 8 and WO 88/07045) (112 mg, 0.2 mmol) was dissolved in 2 ml of dimethylformamide, and then 195 mg (2 mmol) of ethanolamine hydrochloride and 0.61 ml (4 mmol) of 1,8-diazabicyclo[5,4,0]-7-undecene were added thereto, followed by stirring at room temperature for 3 days. After evaporation of the solvent, the residue was subjected to silica gel column chromatography (chloroform/methanol=98/2) to give 75 mg (yield 25%) of Compound I-15.

The following characteristic values may be obtained by using NMR and MS:

$^1$H-NMR (CDCl$_3$+DMSO-d$_6$; 4/1) δ (ppm): 2.23(3H, s), 4.72(1H, t, J=5.0 Hz), 4.90(1H, t, J=5.0 Hz), 5.41(1H, s), 6.89(1H, m), 7.32 –8.10 (6H, m), 9.18(1H, d, J=7.0 Hz), 9.36(1H, d, J=7.0 Hz)

SIMS (m/z): 498 (M+1)$^+$

Compound (J) (see FIG. 8 and Japanese Published Unexamined Patent Application No. 155285/87) (890 mg, 1.5 mmol) was dissolved in 10 ml of dimethylformamide, and then 1.43 g (15 mmol) of ethylamine hydrochloride and 2.28 ml (15 mmol) of 1,8 -diazabicyclo [5,4,0]-7-undecene were added thereto, followed by stirring at room temperature for 2.5 hours. To the solution was added 10 ml of water and the precipitates were collected by filtration to give 729 mg of Compound (K). See FIG. 8.

The following characteristic values may be obtained using NMR:

¹H-NMR (DMSO-d₆) δ (ppm): 1.32(3H, t), 2.00–2.32(1H, m), 2.16(3H, s), 2.96–3.60 (5H, m), 5.00 (2H, s), 7.00–7.76 (6H, m), 8.02 (2H, t, J=8.0 Hz), 8.58(1H, s), 9.18(1H, d, J=8.0 Hz)

Compound (K) (650 mg, 1.39 mmol) was dissolved in 7 ml of dimethylformamide, and then 675 mg (4.16 mmol) of carbonyldiimidazole was added thereto, followed by stirring for 3.5 hours under ice cooling. After 10 ml of water was added to the solution, the precipitates were collected by filtration and subjected to silica gel column chromatography (chloroform/methanol=97/3) to given 395 mg (yield 58%) of Compound (L). See FIG. 8.

The following characteristic values may be obtained using NMR:

¹H-NMR (CDCl₃) δ (ppm): 1.30(3H, t, J=7.0 Hz), 2.30(2H, s), 2.68–2.96 (2H, m), 3.44 (2H, q, J=7.0 Hz), 3.64(1H, d, J=9.0 Hz), 4.09(1H, d, J=9.0 Hz), 4.97(2H, s), 6.45(1H, brs), 6.76(1H, m), 7.20–8.08 (7H, m), 9.32(1H, d, J=8.0 Hz)

Chromic acid (0.49 g, 4.9 mmol) was added to 4 ml of pyridine under ice cooling, and then 2 ml of pyridine containing 345 mg of Compound (L) was added thereto, followed by stirring at room temperature for 12 hours. After the solution was filtered through Celite, the solvent was evaporated, and the residue was recrystallized from chloroform/methanol to give 272 mg (yield 77%) of Compound I-21.

The following characteristic values may be obtained by using NMR:

¹H-NMR (DMSO-d₆) δ (ppm): 1.22(3H, t, J=7.0 Hz), 2.28–2.80(1H, m), 2.36(3H, s), 3.12–3.60(3H, m), 3.86(1H, brd, J=10.0 Hz), 4.22(1H, brd, J=10.0 Hz), 7.16–8.00 (6H, m), 9.04(1H, d, J=8.0 Hz), 9.23(1H, d, J=8.0 Hz)

Preparation of Compounds I-22, I-23, I-24, and I-25

The preparation of compound I-22 has been described (Murakata et al., U.S. Pat. No. 4,923,986). The preparation of compounds I-23 and I-25 has been described in Japanese Published Unexamined Patent Application No. 295588/88. The preparation of Compound 1-24 is as follows:

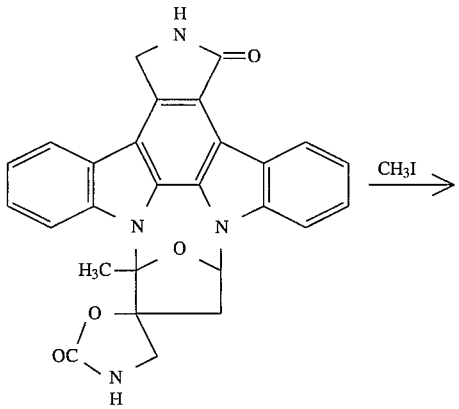

Compound M

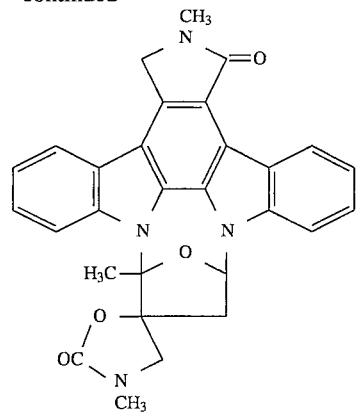

Compound I-24

Compound M (Japanese Published Unexamined Patent Application No. 155285/87) (1 g, 2.2 mmol) was dissolved in 30 ml of dimethylformamide, and then 0.68 ml (11 mmol) of methyl iodide and 3 ml of a 20% aqueous solution of potassium hydroxide were added thereto, followed by stirring at room temperature for 20 minutes. Water was added to the reaction mixture, and the precipitates were collected by filtration and subjected to silica gel column chromatography (2% methanol/chloroform) to give 204 mg (yield 19%) of Compound I-24.

¹H-NMR (DMSO-d₆) δ (ppm): 2.34(3H, s), 2.88(3H, s), 3.12–3.56 (2H, m), 3.82(1H, d, J=10 Hz), 4.16(1H, d, J=10 Hz), 5.08 (2H, s), 7.12–8.12 (8H, m), 9.18(1H, d, J=8 Hz)

Preparation of Compounds III-1 and III-2

The preparation of compounds III-1 and III-2 has been described (Japanese Published Unexamined Patent Application No. 247056/93).

While the invention has been disclosed in considerable detail, it is to be understood that equivalents and modifications which are in the purview of the skilled artisan are considered to be part of this disclosure and the claims that follow.

We claim:

1. A method for enhancing a neurotrophin-induced activity of a neurotrophin responsive cell, said method comprising contacting said cell with a K-252a derivative of the formula:

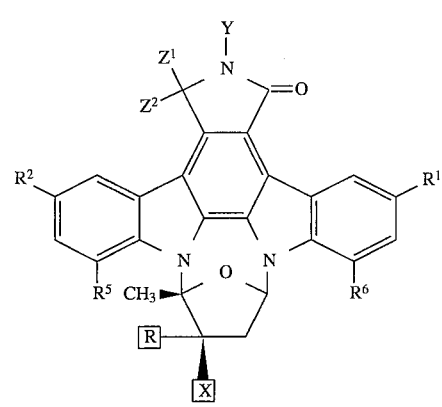

wherein:
 a) $Z^1$ and $Z^2$ together represent O; each $R^1$, $R^2$, $R^5$, and $R^6$ independently is H, F, Cl, Br, I, $NO_2$, CN, alkyl of 1–6 carbons or $NR^{13}R^{14}$ independently is H or n-alkyl of 1–6 carbons;

Y is H, OH, $NH_2$, n-alkyl of 1–6 carbons, CHO, $OCONH_2$ benzyl,

O-n-alkyl of 1–6 carbons, $(CH_2)_nOH$ or $(CH_2)_nNH_2$ where n is an integer of 1–6; then either 1) R is OH, $OCONH_2$, or O-n-alkyl of 1–6 carbons; and X is $CH_2OH$, $CH_2NH_2$, (or an acid salt thereof;) $CH_2$O-n-alkyl of 2–7 carbons $CO_2R^7$ where $R^7$ is H or alkyl of 1–6 carbons, $CONHOR^8$, $CONH(CH_2)_nOR^8$ where n is an integer of 1–6 and $R^8$ is H or an acyl derivative group, or $CONHR^9$ where $R^9$ is alkyl of 1–3 carbons; or 2) R and X are combined to form a linking group of the formula —$CH_2OCR^{10}R^{11}O$— where each $R^{10}$ and $R^{11}$ independently is H or alkyl of 1–3 carbons; or —$CH_2NR^{12}CO_2$— where $R^{12}$ is H or alkyl of 1–3 carbons;

or
 b) $Z^1$ is H and $Z^2$ is OH;
 Y is H or CHO;
 R is OH; and
 X is $CONH(CH_2)_2OH$, $CO_2CH_3$, or $CH_2OH$; and
 $R^1$, $R^2$, $R^5$ and $R^6$ are as defined in a);
or
 c) $Z^1$ and $Z^2$ are both H and R, Y and X are as defined in b), except that X cannot be $CO_2CH_3$; and when $R^1$ is Br, X cannot be $CH_2OH$; and $R^1$, $R^2$, $R^5$ and $R^6$ are as defined in a);
or
 d) $Z^1$ is H and $Z^2$ is $SR^{15}$ where $R^{15}$ is n-alkyl of 1–3 carbons; and Y, R and X are defined as in b), except that when $R^{15}$ is $C_2H_5$, X cannot be $CH_2OH$; and $R^1$, $R^2$, $R^5$ and $R^6$ are as defined in a).

2. A method for enhancing a neurotrophin-induced activity of a neurotrophin responsive cell, said method comprising contacting said cell with a K-252a derivative of the formula:

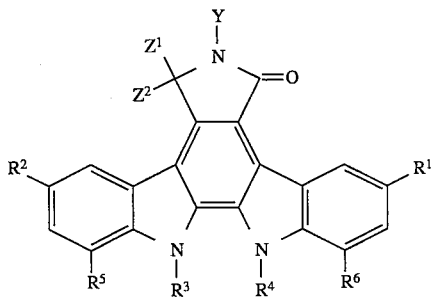

wherein:
 a) when $Z^1$ and $Z^2$ together represent O, then either 1) each $R^1$, $R^2$, $R^5$, and $R^6$ independently is H, F, Cl, Br, I, $NO_2$, CN, alkyl of 1–6 carbons, or $NR^{13}R^{14}$ where each $R^{13}$ and $R^{14}$, independently, is H or n-alkyl of 1–6 carbons; and Y is H, OH, $NH_2$, n-alkyl of 1–6 carbons, CHO, benzyl, O-n-alkyl of 1–6 carbons, $(CH_2)_nOH$ or $(CH_2)_nNH_2$ where n is an integer of 1–6; and each $R^3$ and $R^4$ independently is H or $(CH_2)_nCH(OH)CH_2OH$, where n is an integer of 1–6;

or 2) each $R^1$, $R^2$, $R^3$, $R^4$, $R^5$ and $R^6$ independently is H; and Y is as defined in a) 1), except that Y cannot be benzyl;

or
 b) $Z^1$ is H and $Z^2$ is H, OH, or $SR^{15}$, where $R^{15}$ is n-alkyl of 1–3 carbons;
 Y is H or CHO; and
 each $R^1$, $R^2$, $R^3$, $R^4$, $R^5$, $R^6$ is H.

3. A method for enhancing a neurotrophin-induced activity of a neurotrophin responsive cell, said method comprising contacting said cell with a K-252a derivative of the formula:

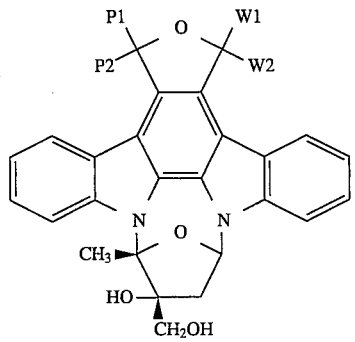

wherein:
 a) each P1 and P2 is H or P1 and P2 together represent O; and each W1 and W2 is H or W1 and W2 together represent O; provided that each P1 and P2 is different from W1 and W2.

4. The method of claim 1, further comprising contacting said cell with an exogenous neurotrophin.

5. The method of claim 4, wherein said neurotrophin is NT-3.

6. The method of claim 2 further comprising contacting said cell with an exogenous neurotrophin.

7. The method of claim 6, wherein said neurotrophin is NT-3.

8. The method of claim 3 further comprising contacting said cell with an exogenous neurotrophin.

9. The method of claim 8 wherein said neurotrophin is NT-3.

* * * * *

UNITED STATES PATENT AND TRADEMARK OFFICE
CERTIFICATE OF CORRECTION

PATENT NO. : 5,516,772

DATED : May 14, 1996

INVENTOR(S) : Marcie A. Glicksman, Robert L. Hudkins, David P. Rotella, Nicola T. Neff, and Chikara Murakata It is certified that error appears in the above-indentified patent and that said Letters Patent is hereby corrected as shown below:

On the title page: Item [54]

"K-252<u>a</u> DERIVATIVES WHICH ENHANCE NEUROTROPHIN-INDUCED ACTIVITY";

Col. 1, line 2, replace the title with "K-252<u>a</u> DERIVATIVES WHICH ENHANCE NEUROTROPHIN-INDUCED ACTIVITY";

Col. 3, line 44, correct the spelling of "ischemia";

Col. 5, line 50, replace "$CH_2OH$" with --$CH_2OH$--; same line, replace "$CH_2NH$" with --$CH_2NH_2$--;

Col. 6, line 2, replace "Zis" with --$Z^1$--;

Col. 6, line 25, replace "$R^{15}$ is CH," with --$R^{15}$ is $C_2H_5$--;

Col. 6, line 44, replace "NO" with --$NO_2$--;

Col. 7, in the formula, replace "$CH_3$" with --CHO--;

Col. 10, line 48, correct the spelling of "ischemia";

UNITED STATES PATENT AND TRADEMARK OFFICE
CERTIFICATE OF CORRECTION

PATENT NO. : 5,516,772

DATED : May 14, 1996

INVENTOR(S) : Marcie A. Glicksman, Robert L. Hudkins, David P. Rotella Nicola T. Neff, and Chikara Murakata It is certified that error appears in the above-indentified patent and that said Letters Patent is hereby corrected as shown below:

Col. 11, line 21, replace "auryl" with --lauryl--;

Col. 14, line 48, replace "(6 M)" with --(6 $\mu$M)--;

Col. 17, line 61, correct the spelling of "*Antibiotics*";

Col. 18, line 13, "(ppm)(: 5.298(2H, s)," should read --(ppm): 5.298(2H, s),--;

Col. 25, claim 1, line 4, after "$NR^{13}R^{14}$", insert --where each $R^{13}$ and $R^{14}$--;

UNITED STATES PATENT AND TRADEMARK OFFICE
CERTIFICATE OF CORRECTION

PATENT NO. : 5,516,772

DATED : May 14, 1996

INVENTOR(S) : Marcie A. Glicksman, Robert L. Hudkins, David P. Rotella, Nicola T. Neff, and Chikara Murakata It is certified that error appears in the above-indentified patent and that said Letters Patent is hereby corrected as shown below:

Col. 25, claim 1, delete lines 30-33, and substitute the following:

--c) $Z^1$ and $Z^2$ are both H and Y is H, CHO, n-alkyl of 1-6 carbons or $OCONH_2$; then either 1) R is OH, O-n-alkyl of 1-6 carbons or $OCONH_2$, except that when Y is H, R is OH; and X is $CONHOR^8$, $CONH(CH_2)_nOR^8$, where n is an integer of 1-6 carbons, $CH_2OH$, or $CO_2CH_3$, except that when Y is H and $R^1$, $R^2$, $R^5$ and $R^6$ are each H, X cannot be $CO_2CH_3$; or 2) R and X are combined to form a linking group of the formula $-CH_2NR^{12}CO_2-$; and each $R^1$, $R^2$, $R^5$ and $R^6$ are as defined in a), except that when $R^1$ is Br, X cannot be $CH_2OH$;--.

Signed and Sealed this

Twelfth Day of November, 1996

Attest:

BRUCE LEHMAN

*Attesting Officer*  *Commissioner of Patents and Trademarks*